(12) United States Patent
Ghasemzadeh et al.

(10) Patent No.: US 10,078,733 B2
(45) Date of Patent: Sep. 18, 2018

(54) SYSTEM AND METHODS FOR NUTRITION MONITORING

(71) Applicant: Washington State University, Pullman, WA (US)

(72) Inventors: Hassan Ghasemzadeh, Moscow, ID (US); Niloofar Hezarjaribi, Pullman, WA (US)

(73) Assignee: WASHINGTON STATE UNIVERSITY, Pullman, WA (US)

( * ) Notice: Subject to any disclaimer, the term of this patent is extended or adjusted under 35 U.S.C. 154(b) by 0 days.

(21) Appl. No.: 15/636,852

(22) Filed: Jun. 29, 2017

(65) Prior Publication Data

US 2018/0004913 A1    Jan. 4, 2018

Related U.S. Application Data

(60) Provisional application No. 62/357,205, filed on Jun. 30, 2016.

(51) Int. Cl.
*G16H 20/60* (2018.01)
*G06F 19/00* (2018.01)
*A23L 33/00* (2016.01)
*A61B 5/00* (2006.01)
*G10L 13/08* (2013.01)

(52) U.S. Cl.
CPC .......... *G06F 19/3475* (2013.01); *A23L 33/30* (2016.08); *A61B 5/48* (2013.01); *G16H 20/60* (2018.01); *G10L 13/08* (2013.01)

(58) Field of Classification Search
CPC .................................................... G16H 20/60
See application file for complete search history.

(56) References Cited

U.S. PATENT DOCUMENTS 9,911,920 B2 *   3/2018   Bulliard ............. H01L 51/0058
9,955,869 B2 *   5/2018   Meltzer ..................... A61B 5/01
2018/0001184 A1 *   1/2018   Tran ..................... H04N 5/2257

OTHER PUBLICATIONS

L. E. Burke, S. M. Sereika, E. Music, M. Warziski, M. A. Styn, and A. Stone, "Using instrumented paper diaries to document self-monitoring patterns in weight loss," Contemporary clinical trials, vol. 29, No. 2, pp. 182-193, 2008.

M. K. Matffeldt-Beman, S. A. Corrigan, V. J. Stevens, C. P. Sugars, A. T Dalcin, M. J. Givi, and K. C. Copeland, "Participants evaluation of a weight-loss program," Journal of the American Dietetic Association, vol. 99, No. 1, pp. 66-71, 1999.

N. Hezarjaribi, C. Reynolds, D. Miller, N. Chaytor, and H. Ghasemzadeh, "S2ni: A mobile platform for nutrition monitoring from spoken data," in 38th Annual International Conference of the IEEE Engineering in Medicine and Biology Society. IEEE, 2016.

(Continued)

*Primary Examiner* — Susan McFadden
(74) *Attorney, Agent, or Firm* — W&C IP

(57) ABSTRACT

An apparatus comprising a natural language processor, a mapper, a string comparator, a nutrient calculator, and a diet planning module, the diet planning module configured to generate a diet action control, the diet action control comprising instructions to operate the client device to perform a diet change recommendation on the client device, and apply the diet action control to the client device.

11 Claims, 17 Drawing Sheets

(56) References Cited

OTHER PUBLICATIONS

Y. Dong, "Tracking wrist motion to detect and measure the eating intake of free-living humans," Ph.D. dissertation, Clemson University, 2012.

Y. Dong, J. Scisco, M. Wilson, E. Muth, and A. Hoover, "Detecting periods of eating during free-living by tracking wrist motion," Biomedical and Health Informatics, IEEE Journal of, vol. 18, No. 4, pp. 1253-1260, 2014.

C. K. Martin, H. Han, S. M. Coulon, H. R. Allen, C. M. Champagne, and S. D. Anton, "A novel method to remotely measure food intake of freeliving individuals in real time: the remote food photography method," British Journal of Nutrition, vol. 101, No. 03, pp. 446-456, 2009.

K. Yatani and K. N. Truong, "Bodyscope: a wearable acoustic sensor for activity recognition," in Proceedings of the 2012 ACM Conference on Ubiquitous Computing. ACM, 2012, pp. 341-350.

H. He, F. Kong, and J. Tan, "Dietcam: Multi-view food recognition using a multi-kernel svm," 2015.

M. M. Anthimopoulos, L. Gianola, L. Scarnato, P. Diem, and S. G. Mougiakakou, "A food recognition system for diabetic patients based on an optimized bag-of-features model," Biomedical and Health Informatics, IEEE Journal of, vol. 18, No. 4, pp. 1261-1271, 2014.

N. Alshurafa, H. Kalantarian, M. Pourhomayoun, J. J. Liu, S. Sarin, B. Shahbazi, and M. Sarrafzadeh, "Recognition of nutrition intake using time-frequency decomposition in a wearable necklace using a piezoelectric sensor," Sensors Journal, IEEE, vol. 15, No. 7, pp. 3909-3916, 2015.

E. S. Sazonov and J. M. Fontana, "A sensor system for automatic detection of food intake through non-invasive monitoring of chewing," IEEE sensors journal, vol. 12, No. 5, pp. 1340-1348, 2012.

E. Thomaz, I. Essa, and G. D. Abowd, "A practical approach for recognizing eating moments with wrist-mounted inertial sensing," in Proceedings of the 2015 ACM International Joint Conference on Pervasive and Ubiquitous Computing. ACM, 2015, pp. 1029-1040.

J. Cheng, B. Zhou, K. Kunze, C. C. Rheinländer, S. Wille, N. Wehn, J. Weppner, and P. Lukowicz, "Activity recognition and nutrition monitoring in every day situations with a textile capacitive neckband," in Proceedings of the 2013 ACM conference on Pervasive and ubiquitous computing adjunct publication. ACM, 2013, pp. 155-158.

G. Ciocca, P. Napoletano, and R. Schettini, "Food recognition and leftover estimation for daily diet monitoring," in New Trends in Image Analysis and Processing—ICIAP 2015 Workshops. Springer, 2015, pp. 334-341.

J. Chae, I. Woo, S. Kim, R. Maciejewski, F. Zhu, E. J. Delp, C. J. Boushey, and D. S. Ebert, "Volume estimation using food specific shape templates in mobile image-based dietary assessment," in IS&T/SPIE Electronic Imaging. International Society for Optics and Photonics, 2011, pp. 78 730K-78730K.

S. S. Intille, C. Kukla, R. Farzanfar, and W. Bakr, "Just-in-time technology to encourage incremental, dietary behavior change," in AMIA Annual Symposium Proceedings, vol. 2003. American Medical Informatics Association, 2003, p. 874.

C. C. Tsai, G. Lee, F. Raab, G. J. Norman, T. Sohn, W. G. Griswold, and K. Patrick, "Usability and feasibility of pmeb: a mobile phone application for monitoring real time caloric balance," Mobile networks and applications, vol. 12, No. 2-3, pp. 173-184, 2007.

J. J. Rodrigues, I. M. Lopes, B. M. Silva, and I. d. L. Torre, "A new mobile ubiquitous computing application to control obesity: Sapofit," Informatics for Health and Social Care, vol. 38, No. 1, pp. 37-53, 2013.

B. Ballinger, C. Allauzen, A. Gruenstein, and J. Schalkwyk, "Ondemand language model interpolation for mobile speech input." In Interspeech, 2010, pp. 1812-1815.

M. Korpusik, C. Huang, M. Price, and J. R. Glass, "Distributional semantics for understanding spoken meal descriptions," in 2016 IEEE International Conference on Acoustics, Speech and Signal Processing, ICASSP 2016, Shanghai, China, Mar. 20-25, 2016, 2016, pp. 6070-6074. [Online]. Available: http://dx.doi.org/10.1109/ICASSP.2016.7472843.

* cited by examiner

SYSTEM AND METHODS FOR NUTRITION MONITORING

CROSS-REFERENCE TO RELATED APPLICATIONS

This application claims benefit under 35 U.S.C. 119 to U.S. application Ser. No. 62/357,205, filed on Jun. 30, 2016, and incorporated herein by reference in its entirety.

BACKGROUND

The prevalence of chronic disease and health-care costs associated with conditions such as diabetes, cardiovascular disease, cancer, and obesity continue to rise nationally and worldwide. One reason is the absence of proper balance between calorie intake and energy expenditure. In addition to balancing calorie intake and physical activity, a special diet for cardiovascular disease and diabetes has been proposed by the American Heart Association. As a result, interventions that help with prevention or self-management of chronic diseases play a central role in reducing health-care costs as well as mortality and morbidity rates.

Self-monitoring is one of the earliest techniques in this field, involving meal recalls and food frequency questionnaires. This conventional technique suffers from several limitations including biases to memory, low adherence, and labor-intensiveness. Other conventional techniques in this area can be divided into three main categories: (1) wearable sensors, (2) computer vision, and (3) smart-phone apps.

Utilizing wearable sensors require individuals to wear specialized devices, which results in limitation in their practicality. A main weakness in using computer vision for diet monitoring is time sensitivity. The image-based nature of this technique requires data recording prior to nutrition intake. Moreover, this technique utilizes existing web images, which do not represent real world data.

The main challenge in nutrition monitoring is to provide users with real-time nutrition intake information, which is not provided by most of the conventional techniques. Although the above technologies provide user with feedback about the nutrition intake, they still require manually recording the data by the end-user.

BRIEF SUMMARY

The present system and method provide: (1) a new framework for voice-based nutrition monitoring and a hierarchy of data processing modules including speech recognition, natural language processing, and text analysis, in order to extract nutrient information from spoken language, and (2) a 2-tier string search algorithms including an exact matching and an edit-distance based approximation matching to search food items from a nutrition database and to compute nutrient information.

The present system and method provide a 2-layer approach for analyzing the identified text to compute nutrition intake. Results show that performance of the speech-to-text (S2T) application is 66.50%. For extracting the nutrition specific data from the S2T output, the natural language processing (NLP) program may be implemented in a programming language, such as Python. The performance of the string comparator with error-free text is 95%. When the matching algorithm takes the output of the S2T application as input, the calorie intake information is computed with 75% accuracy for a clear environment and 71.36% for a noisy environment. Moreover, a user acceptance test that compared the present system and method with two other nutrition monitoring techniques (text-based and image-based) shows that the present system and method has higher scores in technology adoption metrics than the conventional methods.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
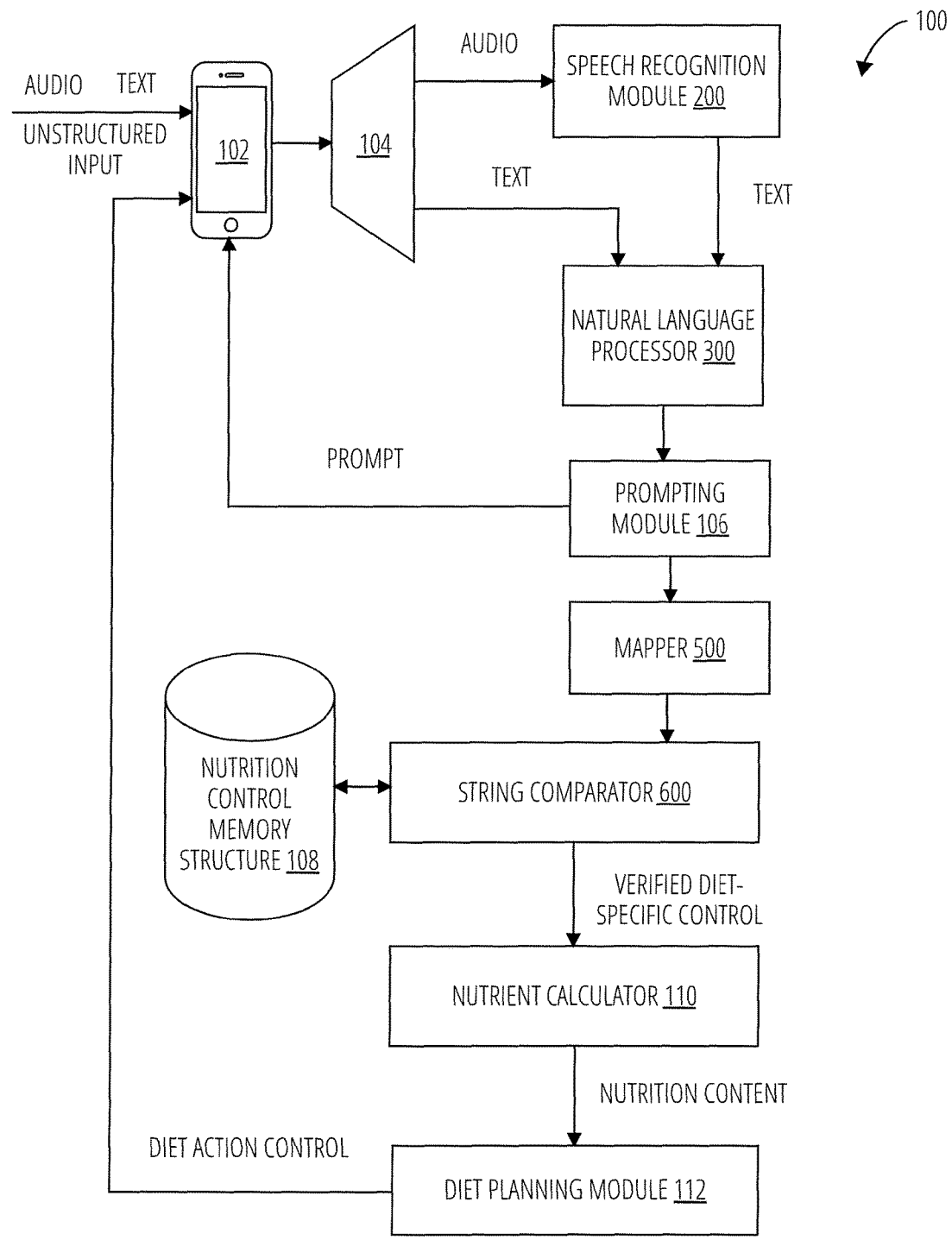
FIG. 1 illustrates an embodiment of a nutritional monitoring and control system 100.

Disclosed herein are embodiments of a novel nutritional monitoring and control system. The system is designed in accordance with experimental results obtained from a user acceptance test survey that includes five categories: attention, interaction, trust, impact, and ranking. Responses are either on a Likert scale from 1-5, or in the form of a ranking. Table 1 demonstrates the findings from the user acceptance test survey.

TABLE 1

| Categories | Voice-Based | Text-Based | Image-Based |
|---|---|---|---|
| Attention | | | |
| How frequently did you use the mobile app? | 3.89 | 3.13 | 2.75 |
| Interaction | | | |
| How satisfied are you with the app's ease of use? | 4.25 | 3.13 | 2.25 |

TABLE 1-continued

| Categories | Voice-Based | Text-Based | Image-Based |
| --- | --- | --- | --- |
| How encouraging was the use of the mobile app? | 3.89 | 3.44 | 2.67 |
| Privacy | | | |
| How satisfied are you with the privacy of using the apps? | 3.56 | 3.75 | 2.38 |
| Impact | | | |
| What number would you use to rate each mobile app? | 2.44 | 2.00 | 1.56 |
| Rating | | | |
| How likely are you going to use S2NI as your nutrition monitoring app? | 3.25 | N/A | N/A |

Attention—Participants were the most active accessing their phone during the usage of voice-based technique, on average 7 times per day and weighted average recorded in survey was 3.89/5. Data collection using image-based method had the least number of accesses. Moreover, the data using image-based show that most of the participants remembered recording the food intake after they started eating; therefore, it likely cannot be a reliable technique for nutrition monitoring.

Interaction—Two questions were provided in this category. The first asked about the ease-of-use of each method. The second question asked how frustrating the methods are. The voice-based method was not only easy to use (4.25/5), but also encouraging (3.89/5) compared to the other two techniques. Image-based was neither easy to use (2.25/5) nor encouraging (2.67/5).

Privacy—Participants felt text-based method is more private (3.75/5) than other two techniques. Voice-based users felt uncomfortable to record their food in public; likewise, users were not willing to take an image from their food most of the time due to the appearance of the dish.

Impact—Based on the survey, 75% of participants considered voice-based, 25% text-based, and 0% image-based as the best method. With the scale of 1-3 where 3 was the highest and 1 was the lowest number, voice-based, text-based, and image-based had weighted averages of 2.44, 2.00, and 1.56, respectively.

Ranking—Participants were asked to rank voice-based (S2NI) individually with the scale of 1-5. Four people implied they are going to use the app very likely, 2 somewhat likely, and 4 somewhat unlikely.

Referring to FIG. 1, an embodiment of a nutritional monitoring and control system 100 in accordance with these survey results comprises a client device 102, a device signal switch 104, a prompting module 106, a nutrition control memory structure 108, a nutrient calculator 110, a diet planning module 112, a speech recognition module 200, a natural language processor 300, a mapper 500, and a string comparator 600.

The client device 102 receives a text input or an audio input. The client device 102 sends the text input or the audio input to the device signal switch 104. The client device 102 may also receive a prompt from the prompting module 106. In response to the prompt, the client device 102 is configured to receive an unstructured input. Further, the client device 102 may receive a diet action control from the diet planning module 112. The client device 102 may operate, in response to the diet action control, to alter the machine display or provide a machine response, such as a vibration, sound, audio, etc.

The device signal switch 104 receives the text, the audio, and the unstructured input from the client device 102 and determines whether that unstructured input is audio or text. The device signal switch 104 sends audio to the speech recognition module 200 and text to the natural language processor 300.

The speech recognition module 200 receives the audio from the device signal switch 104. The speech recognition module 200 converts the audio to text. In one embodiment, Google™'s voice recognition engine is utilized to convert the audio to text. The nutritional monitoring and control system 100 may store the text output in a text file for further analysis. The speech recognition module 200 then sends the text to the natural language processor 300. The speech recognition module 200 is further described in FIG. 2.

The natural language processor 300 receives the text from the device signal switch 104 or the speech recognition module 200. The natural language processor 300 transforms the text into a generated entity or a prompt activation signal, based on the text received. A text received in response to a prompt is utilized to modify a previously received text to help transform the text into the generated entity. The natural language processor 300 may split the text into one or more sentences, tokenize each of the sentences, and perform Part of Speech tagging on each token in each sentence. A programming language, such as Python, may be utilized to implement these functions. The natural language processor 300 then sends the generated entity or the prompt activation signal to the prompting module 106. The natural language processor 300 is further described in FIG. 3, and may be operated in accordance with the process embodiment depicted in FIG. 9.

The prompting module 106 receives the generated entity or the prompt activation signal from the natural language processor 300. The prompting module 106 determines which signal has been received and sends a prompt to the client device 102, the prompt comprising instructions to operate the client device 102 to further receive an unstructured input, and sends the generated entity to the mapper 500. For example, if the prompting module 106 receives a prompt activation signal indicating that the time could not be determined from the text by the natural language processor 300, the prompting module 106 sends a prompt to operate the client device 102 to query the time that the action associated with the text occurred (e.g., displaying on the client device 102, "When did you eat?"). The prompting module 106 may be operated in accordance with the process embodiment depicted in FIG. 10.

The mapper 500 receives the generated entity from the prompting module 106, transforms the generated entity to mapped data lists, and sends the mapped data lists to the string comparator 600. The mapper 500 is further described in FIG. 5, and may be operated in accordance with the process depicted in FIG. 11.

The string comparator 600 receives the mapped data lists from the mapper 500. The string comparator 600 transforms the mapped data lists into a verified diet specific signal utilizing the nutrition control memory structure 108. The string comparator 600 may extract nutrition information for determined food names and portion size in the mapped data lists. A programming language, such as Python, may be utilized to implement the string comparator 600. The string comparator 600 then sends the verified diet-specific control to the nutrient calculator 110.

The nutrition control memory structure 108 comprises food names and their specified nutrient per serving. In one embodiment, the nutrition control memory structure 108 comprises food/nutrient correlations from the United States Department of Agriculture (USDA) national database. The database may be implemented as a dictionary, where food names are keys and nutrient values and portion sizes are the tags. The dictionary is a hash table with the time complexity for accessing the data being of O(1).

The nutrient calculator 110 receives the verified diet-specific control. Then, based on the verified diet-specific control, the nutrient calculator 110 module outputs nutrition content, which may include diet information, such as calories, carbohydrate, protein, sugar, sodium, vitamins, minerals, etc. The following algorithm may be utilized to this end:

$$NI(p_i, u_i, f_i) = NVal(f_i) \times \frac{p_i}{Serv(f_i)} \quad \text{Equation 1}$$

where $Serv(f_i)$ and $NVal(f_i)$ represent Size Per Unit and Nutrient Value based on the verified diet-specific control generated from the nutrition control memory structure 108 and the string comparator 600. $p_i$ and $u_i$ are the size and unit based on the mapped data lists generated by the mapper 500. The calculation is performed for each food name and nutrient value (i.e., calories, carbohydrate, protein, sugar, sodium, vitamins, minerals, etc.). The nutrient calculator 110 sends the nutrition content to the diet planning module 112.

The diet planning module 112 receives the nutrition content from the nutrient calculator 110. The diet planning module 112 transforms the nutrition content into a diet action control. The diet planning module 112 generates diet recommendations based on the sensed diet behavior from the nutrition content (e.g., calorie intake, protein, carbohydrate, etc.) and the diet goal of the individual. An example of a nutrition goal is to achieve the Dietary Reference Intakes recommended by the Food and Nutrition Board, Institute of Medicine, National Academies. The diet planning module 112 may generate a diet change recommendation. The diet planning module 112 determines the change of a user's behavior over time and learns a personalized model of the diet behavior change which is used to make the recommendations. This model of behavior intervention may utilize reinforcement learning.

The sensed diet behavior (e.g., amount of calorie intake) is an indication of the amount of reward in a reinforcement learning problem. The rewards are computed according to user's adherence to the recommended diet change and amount of diet intake with respect to the diet goal. The diet planning module 112 may continue to generate a recommendation based on the likelihood that the user undertakes the recommendation. The diet action control may comprise instruction to operate the client device 102. The diet action control may operate the client device 102 to display the recommendation or generate an alert, such as a text, vibration, audio, or sound. The diet action control may also configure the client device 102 to display an action control, the action control affecting a purchase of a food item associated with the diet action control. In one embodiment, the diet planning module 112 may be operated in accordance with the process depicted in FIG. 13.

Embodiments of the nutritional monitoring and control system 100 were assessed in four different environments: no noise, street noise, music, and movie. Users utilized a client device 102 to input an unstructured input based on a script with a variety of food names. The calorie calculation accuracy was increased utilizing a similarity algorithm embedded in the nutritional monitoring and control system 100. The similarity algorithm attempted to correct errors of the nutritional monitoring and control system 100 and to compensate for incompleteness of database. In addition to finding the most similar food name to the word that the user expressed, the probability of similarity between words in the sentence and the food names in the database was also computed. This probability was compared with a pre-determined threshold value, which was a given input to the algorithm. The accuracy values were calculated for 30 different pre-determined threshold values ranging from 0.7 to 0.99. The results comprise performance of the speech-to-text application with and without presence of noise, and the performance of the calorie calculation using the pre-determined threshold values.

An exemplary algorithm for the nutritional monitoring and control system 100 follows:

---

1: procedure EZNutriPal-algorithm
2: input: Set sentence rawSen = {S1, S2, . . . , Sn} to output of data acquisition unit, simTh
3: Output: NutritionIntake
4: for each si in S do > Sentences obtained from S2T are splitted up using a delimiter
5: [FNList, PSList, UnitList, TSList] NLPUnit(si) > Sentences will be toknized, tagged using Named Entity Recognition (NER)
6: associatedNutrientData SimpleMappingBlock(rawSen, FNList, PSList, UnitList, TSList) > Mapping the obtained nutrient info to their associated food names
7: for eachnutrientDataND in associatedNutrientData do > Food names, portion sizes, units, and time stamps NDValue ValueMappingBlock (ND) > Extracting the corresponding value to each info
8: FoundFNList StringMatchingUnit(FNList) > FoodNames are being searched in database
9: NutritionIntake NutritionCalculatorUnit(NDValue)

---

The nutritional monitoring and control system 100 may utilize Google's open source speech recognition API for the Android™ platform. This API displays a "Speak now" dialog and waits for user input. After user input, the API streams the audio to Google's server, and the API responds using RecognizerIntent. speech.RecognizerIntent.EXTRA_LANGUAGE_MODE informs the speech model to the recognizer while performing ACTION_RECOGNIZE_SPEECH.

Figure 8:
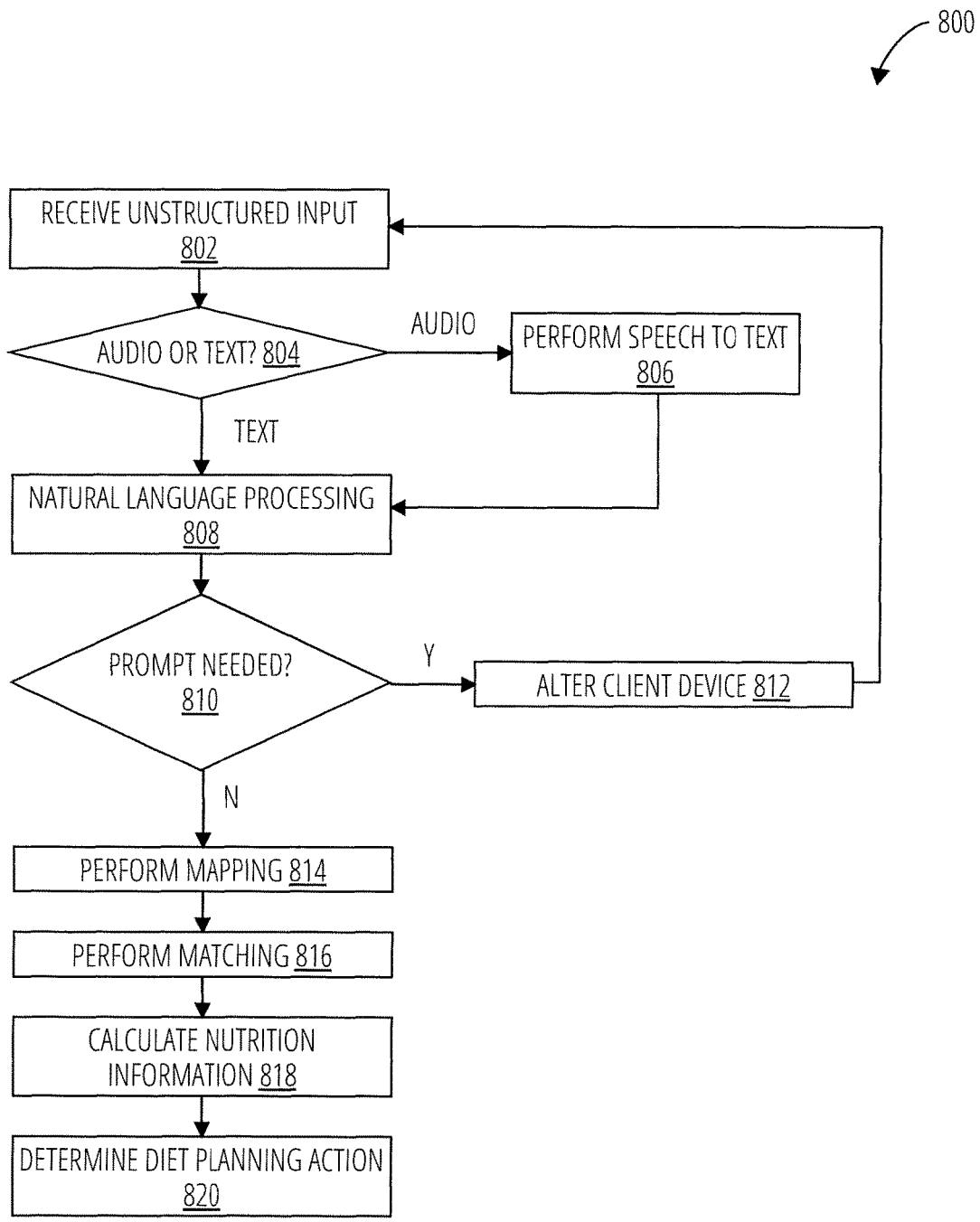
FIG. 8 illustrates an embodiment of a nutrition monitoring and control method 800.

The nutritional monitoring and control system 100 may be operated in accordance with the process embodiment depicted in FIG. 8.

Figure 2:
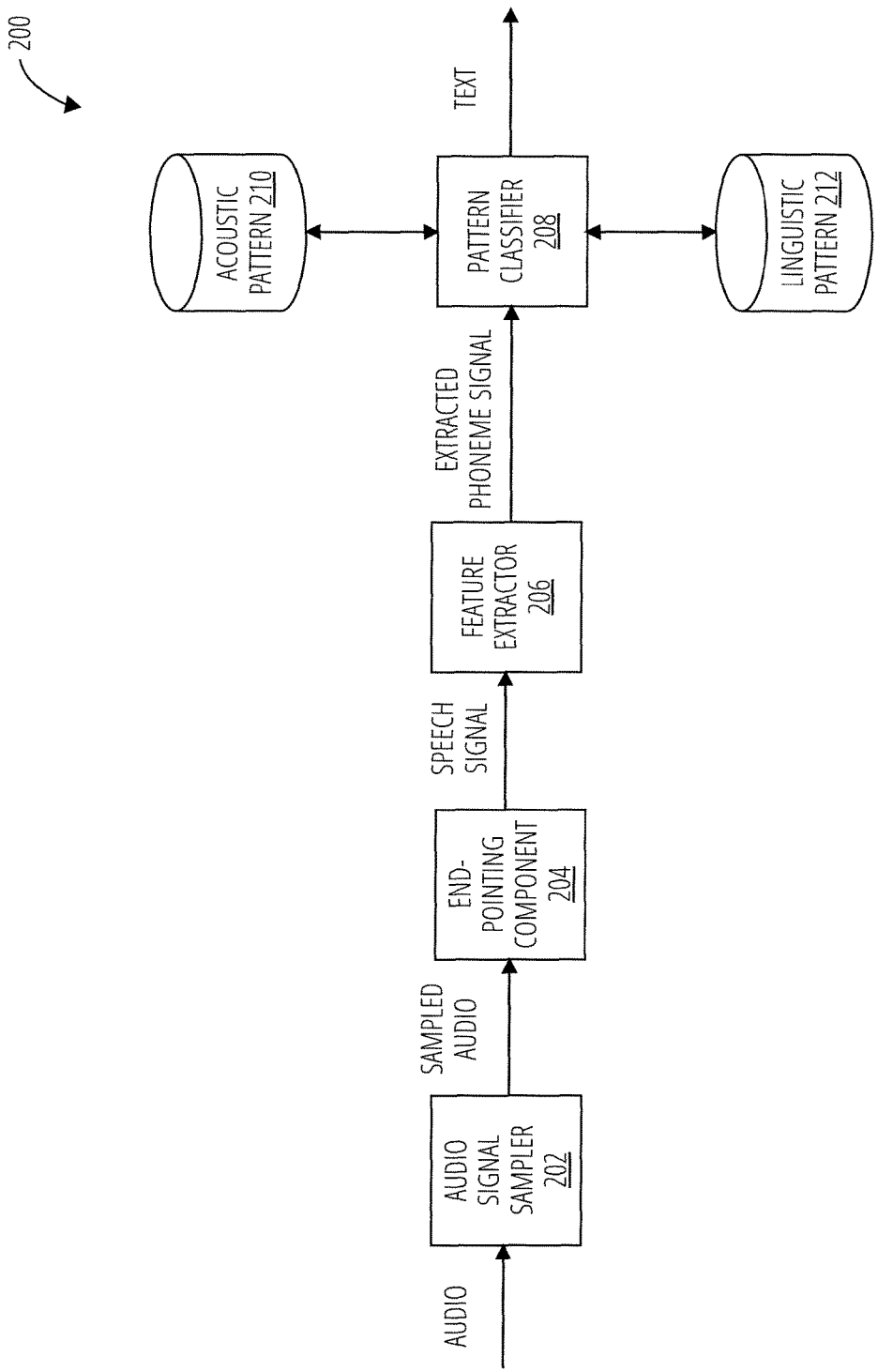
FIG. 2 illustrates an embodiment of a speech recognition module 200.

Referring to FIG. 2, an embodiment of a speech recognition module 200 comprises an audio signal sampler 202, an end-pointing component 204, a feature extractor 206, a pattern classifier 208, an acoustic pattern control memory structure 210, and a linguistic pattern control memory structure 212.

The audio signal sampler 202 receives an audio from the device signal switch 104. The audio signal sampler 202 samples the audio by first generating discrete signal values and then sampled audio signals are generated by digitizing the discrete signal values. The audio signal sampler 202 sends the sampled audio to the end-pointing component 204.

The end-pointing component 204 receives the sampled audio from the audio signal sampler 202. The end-pointing component 204 differentiates between the speech regions and the non-speech regions. This may be performed to decrease computational complexity and prevent hallucination of unspoken words. The end-pointing component 204 then sends the speech signal to the feature extractor 206.

The feature extractor 206 receives the speech signal from the end-pointing component 204. As pattern matching on the raw sample streams is not efficient, the feature extractor 206 extracts features from the audio wave based on where these features lie in the frequency distribution of the speech signal. The feature extractor 206 may eliminate unrelated factors from the input sequence. The speech signal is converted into a time-frequency representation, called a spectrogram, in which phonemes have distinct dominant frequency bands. The feature extractor 206 extracts these phoneme signals. The feature extractor 206 sends the extracted phoneme signals to the pattern classifier 208.

The pattern classifier 208 receives the extracted phoneme signals, as well as acoustic and linguistic pattern templates from the acoustic pattern control memory structure 210 and the linguistic pattern control memory structure 212, respectively.

The pattern classifier 208 matches the extracted phoneme signal to one of the templates based and selects the closest one as the text output. Several pattern classification approaches may be utilized, such as template matching, Hidden Markov Model (HMM), etc. The pattern classifier 208 sends the text to the natural language processor 300.

Table 2 depicts accuracy results for the speech recognition module 200 based on four sound environments: clear sound environment, street noise, music sound, and movie sound.

TABLE 2

| clearEnv | Street | Music | Movie |
|---|---|---|---|
| 73.86% | 63.26% | 64.39% | 64.39 |

Equation 2 depicts the algorithm utilized for Table 2.

$$ACC_{S2T} = \left(\frac{|NSW| - |\overline{NSW}|}{|NSW|}\right) \times 100 \quad \text{Equation 2}$$

where |NSW| is the total number of nutrition specific data in the script and |$\overline{NSW}$| is the total number of incorrectly detected data using the speech recognition module.

Figure 3:
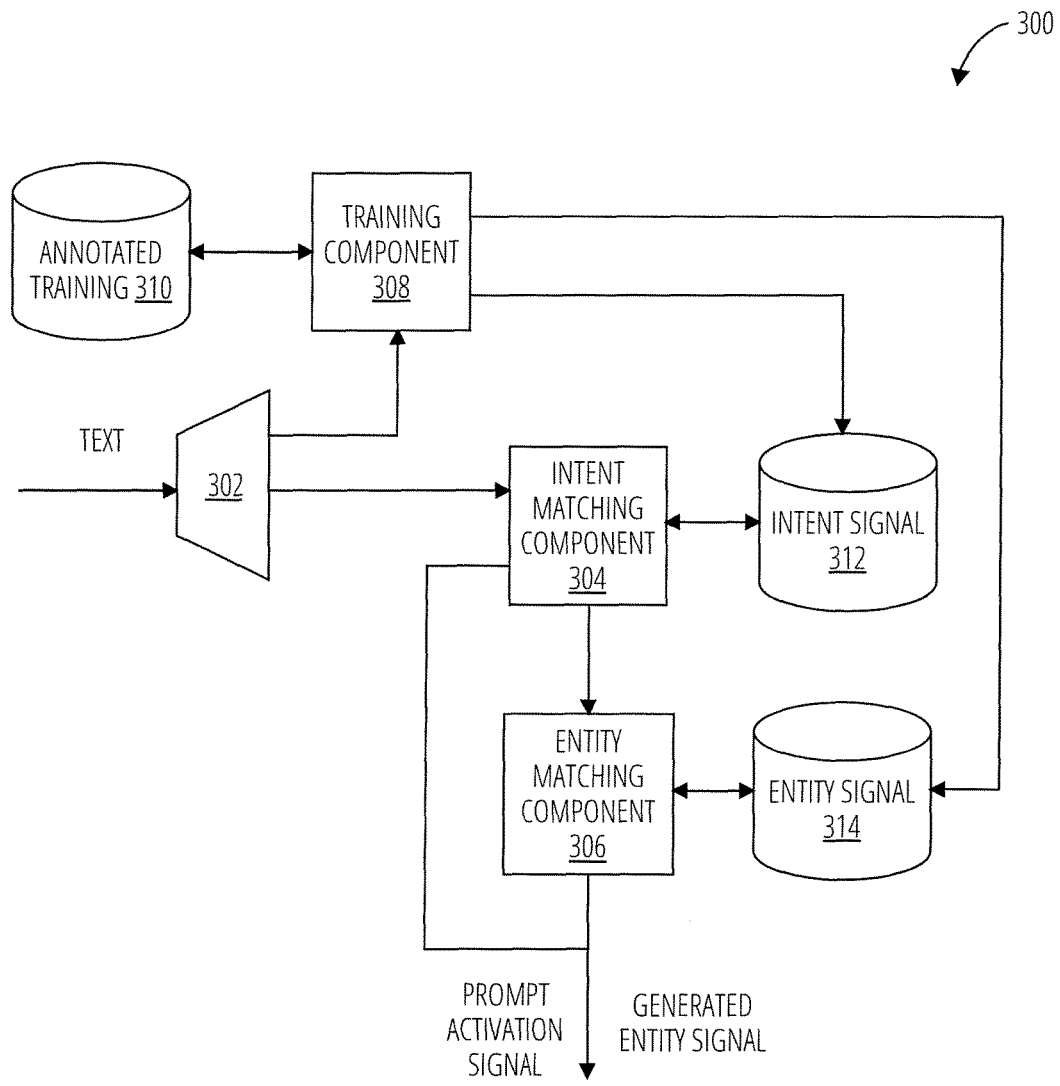
FIG. 3 illustrates an embodiment of a natural language processor 300.

Referring to FIG. 3, an embodiment of a natural language processor 300 comprises a text signal receiver 302, an intent matching component 304, an entity matching component 306, a training component 308, an annotated training control memory structure 310, an intent signal control memory structure 312, and an entity signal control memory structure 314.

Figure 4:
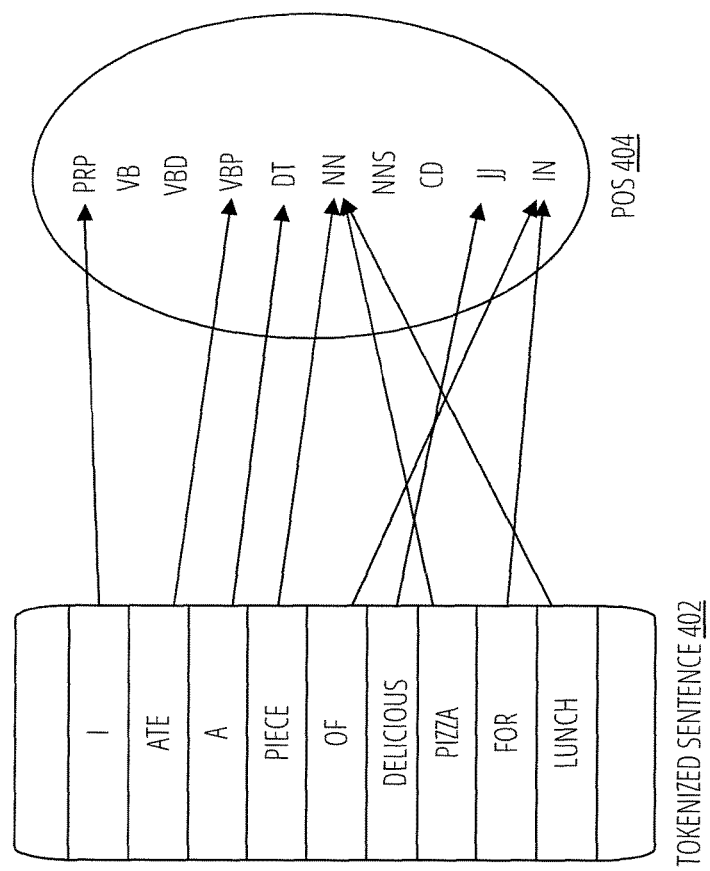
FIG. 4 illustrates an embodiment of a POS tagging 400.

The text signal receiver 302 receives a text from the device signal switch 104 or the speech recognition module 200. The text signal receiver 302 sends the text to the intent matching component 304 and the training component 308. The text signal receiver 302 may tokenize the text prior to sending to the training component 308 and the intent matching component 304. The tokenization enhances the ability to locate the nutrition specific data by utilizing a predefined set of patterns. The sentences broken into a stream of words. Next, each word has a part of speech (POS) tag assigned. These tags may be predefined. A combination of tags may be nutrition-related tags (e.g., NN+NN, VBN+NN, NN+IN+ NN, etc.). FIG. 4 depicts POS tagging that may result from operation of the natural language processor 300.

The intent matching component 304 receives the text from the text signal receiver 302. The intent matching component 304 determines whether there is an intent signal in the intent signal control memory structure 312 that matches the text received from the text signal receiver 302. The intent matching component 304 may send a signal to the intent signal control memory structure 312 to retrieve the intent signals form the intent signal control memory structure 312 to enable a comparison to be made. For example, a text may comprise the statement, "I had a piece of pizza". The intent matching component 304 may determine that the text matches the intent signal, "I had @portionSize @Unit of @foodName for @Time". If an intent signal matches the text, the intent matching component 304 sends the text to the entity matching component 306. If an intent signal is not matched to the text, the intent matching component 304 sends a prompt activation signal to the prompting module 106. The intent matching component 304 may utilize the text received in response to the prompt activation signal to alter the text that activated the prompt activation signal. The intent matching component 304 then matches the updated text to the intent signal.

The entity matching component 306 receives the text from the intent matching component 304. The entity matching component 306 determines the entity signals in the text. For each intent tag (e.g., @portionSize, @Unit, @foodName, and @Time), the entity matching component 306 sends a signal to the entity signal control memory structure 314 to retrieve the list of potential entities. The text is then compared to the list of potential entities. The entity matching component 306 matches the text to one or more entities from the list of potential entities. For example, the entity matching component 306 may match "a":portionSize, "piece":Unit, "pizza":foodName, "null":Time. If no entity is matched, a "null" may be utilized. The entity matching component 306 may also receive a list of required entities. If one of the required entities is not matched (i.e., "null"), the entity matching component 306 sends a prompt activation signal to the prompting module 106. The entity matching component 306 may utilize the text received in response to the prompt activation signal to alter the text that activated the prompt activation signal. The entity matching component 306 then matches the updated text to the list of potential entities. The entity matching component 306 sends a generated entity to the prompting module 106. If any entity is missing, prompting module 106 sends a prompt to client device 102 to query for missing information. Otherwise, the entity matching component 306 sends the generated entity to the mapper 500.

The training component 308 receives the text from the text signal receiver 302. In other embodiments, the training component 308 receives text that generates a prompt activation signal from the intent matching component 304 or the entity matching component 306. The training component 308 may determine intent signals and entity signals from the text and send those to the intent signal control memory structure 312 and the entity signal control memory structure 314. Exemplary changes that may be applied to intent signals and entity signals include: 1) assigning a different entity to an already annotated example (add "breakfast" to list of Time entities in the entity signal control memory structure 314); 2) deleting wrong annotations (remove "apple" from list of Time entities in the entity signal control memory structure 314); 3) adding new entities to entity bank example (add "snack" to Time entities); and 4) adding an unrecognized sentence to the intent bank (add "I ate @portionSize @Unit of @foodName for @time to intent signal control memory structure 312). The training component 308 may receive an input to determine the intent signals and the entity signals. The training component 308 may also receive a training signal from the annotated training control memory structure 310. The training signal comprises intent signals and entity signals to send to the intent signal control memory structure 312 and the entity signal control memory structure 314.

The annotated training control memory structure 310 stores training signals to send to the intent signal control memory structure 312 and the entity signal control memory structure 314. The annotated training control memory structure 310 may receive an input to store the training signal.

The intent signal control memory structure 312 comprises a set of user expressed sentences, which are tagged as nutrition monitoring intents. The nutrient related words of these sentences are tagged. The intent signal control memory structure 312 sends the intent signals to the intent matching component 304 in response to a request from the intent matching component 304.

The entity signal control memory structure 314 comprises one or more entity signals, which are lists per each nutrition specific data (FoodName, PortionSize, Unit, Time). The entity signal control memory structure 314 sends the generated entity signals to the entity matching component 306 in response to a request from the entity matching component 306.

Figure 9:
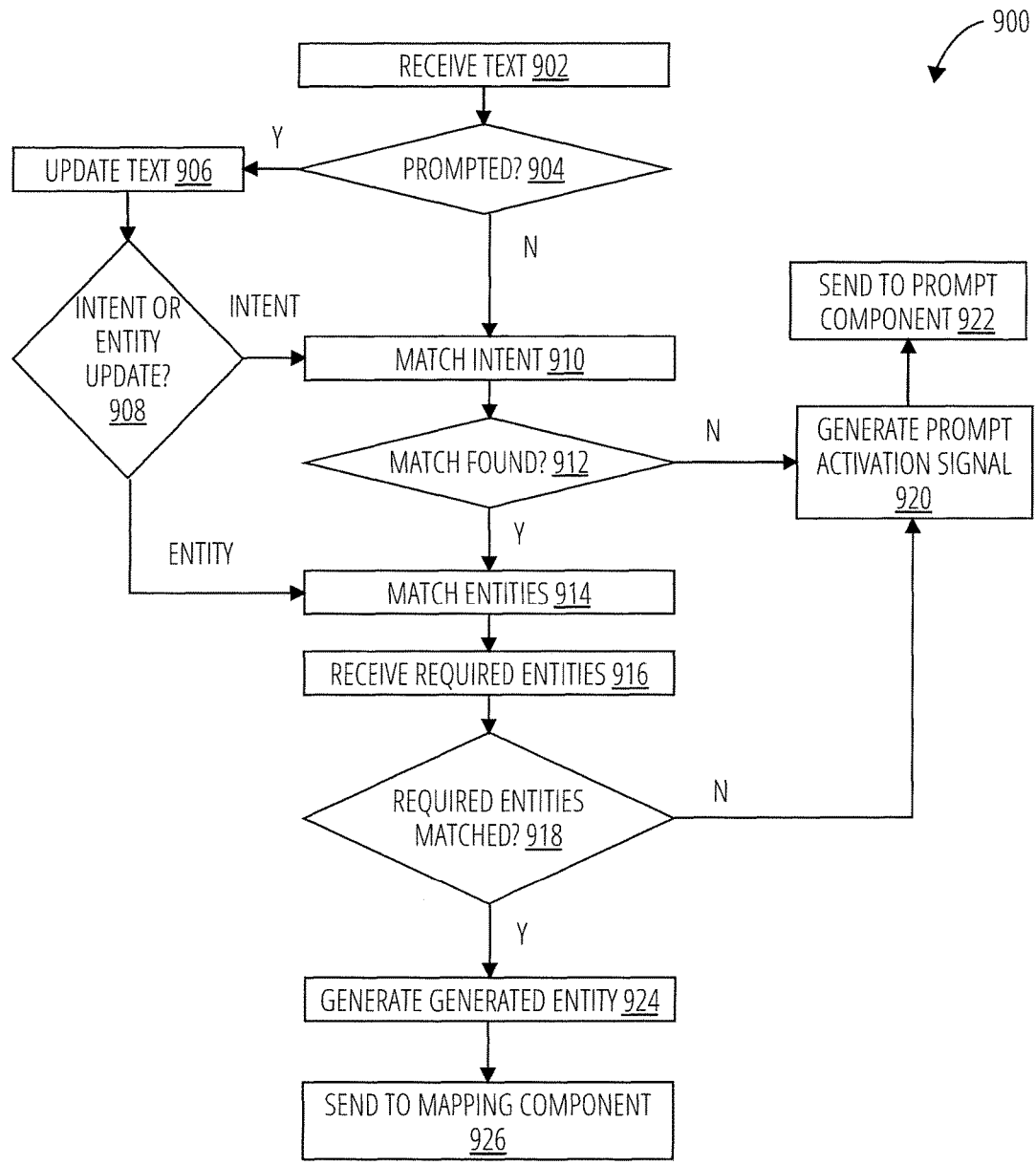
FIG. 9 illustrates an embodiment of an NLP method 900.

The natural language processor 300 may be operated in accordance with the process embodiment depicted in FIG. 9.

Referring to FIG. 4, POS tagging 400 comprises a tokenized sentence 402 and a list of parts of speech tags 404. Each token of the tokenized sentence 402 is matched to a part of speech tag from the list of parts of speech tags 404. An exemplary list of parts of speech tags 404 includes PRP—Personal pronoun; VB—Verb, base form; VBD—Verb, past tense; VBP—Verb, non-3rd person singular present; DT—Determiner; NN—Noun, singular or mass; NNS—Noun, plural; CD—Cardinal number; JJ—Adjective; and IN—Preposition or subordinating conjunction. Each arrow depicted in FIG. 4 represents a token matched to a tag.

Figure 5:
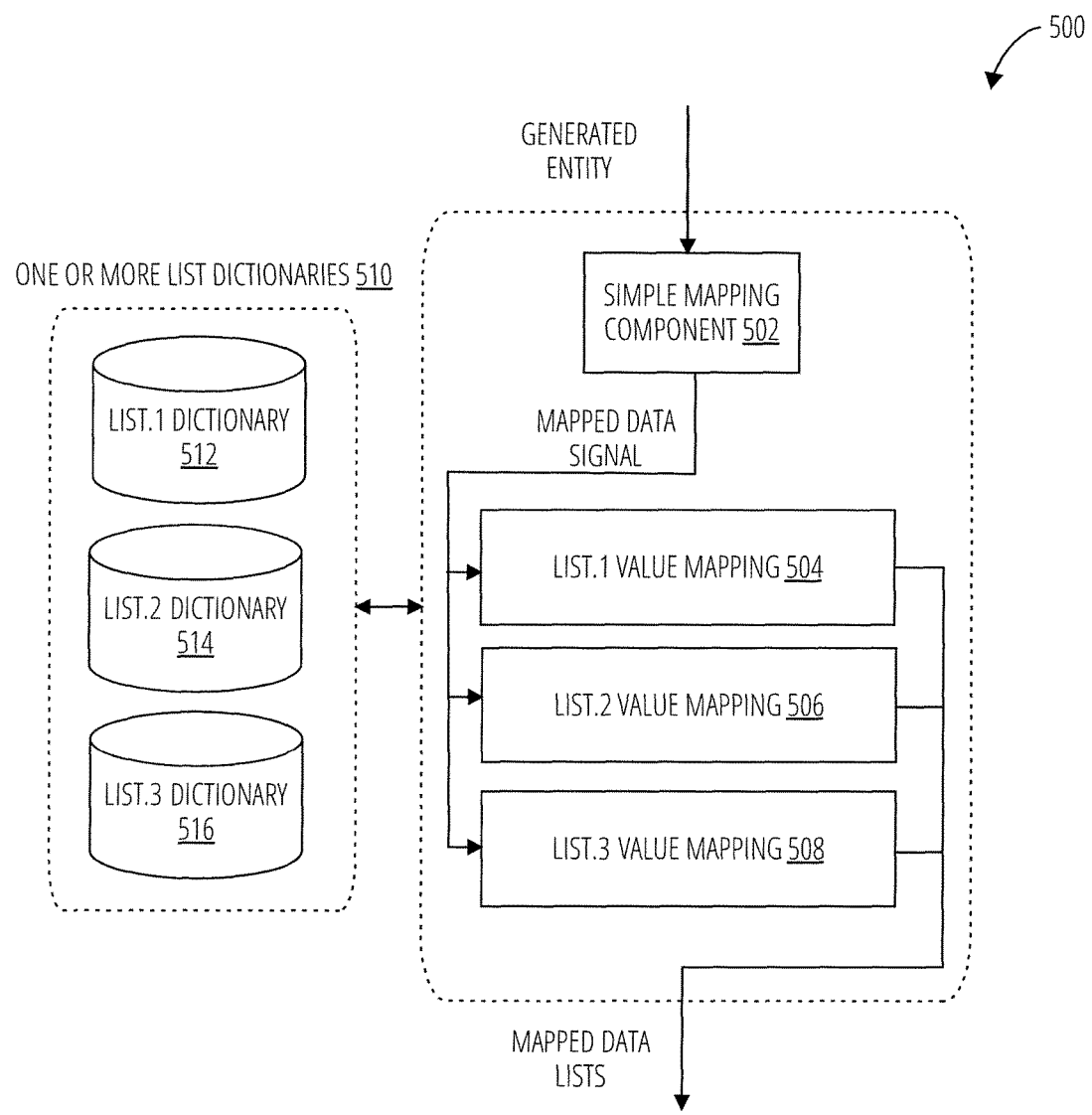
FIG. 5 illustrates an embodiment of a mapper 500.

Referring to FIG. 5, the mapper 500 comprises a simple mapping component 502, a first value mapping component 504, a second value mapping component 506, a third value mapping component 508, and a one or more list dictionaries 510. The one or more list dictionaries 510 further comprises a first dictionary control memory structure 512, a second dictionary control memory structure 514, and a third dictionary control memory structure 516.

The simple mapping component 502 receives the generated entity. The simple mapping component 502 associates entities based on the generated entity and a programmed algorithm, which may be updated by an input. The simple mapping component 502 may utilize the following to associate the entities:
1) If length of the lists are the same, the entities are mapped by the same order they are placed in the lists.
2) The location is determined for each entity with respect to food name (e.g., portion size proceeds food name).
3) The distance of the entities in each list is calculated from the food names. The entity that is located before food name and has the minimum distance is mapped to its associated food name, (e.g., "I had 1 piece of pizza and coke with 2 small french fries."|"1":"piece": "pizza", "defVal":"defVal":"coke", "2":"small": "french fries"). This problem is solved with the Hungarian method.

The simple mapping component 502 then sends the mapped data signal to the first value mapping component 504, the second value mapping component 506, and the third value mapping component 508. The number of value mapping components is the number of entities associated with a food name. As depicted in FIG. 3, the exemplary mapped data signal has three entities associated with a food name ("pizza", "coke", and "French fries"). The lists of associated entities may comprise words that are not recognized by the nutrition control memory structure 108, such as, "few", "some", "ounce", etc. Therefore, the one or more list dictionaries 510 are prepared which map these words to values that are understandable by the nutrition control memory structure 108. Each of the first value mapping component 504, the second value mapping component 506, and the third value mapping component 508 determines the entities associated with food names that are not recognized by the nutrition control memory structure 108 and substitutes an appropriate entity based on the first dictionary control memory structure 512, the second dictionary control memory structure 514, and the third dictionary control memory structure 516. For example, "piece" may not be recognized by the nutrition control memory structure 108. The first dictionary control memory structure 512, the second dictionary control memory structure 514, or the third dictionary control memory structure 516 may represent "pizza" and would comprise the recognized entity, such as "slice". The first value mapping component 504, the second value mapping component 506, or the third value mapping component 508 then makes the appropriate substitution (e.g., "1":"slice":"pizza"). If the generated entity does not comprise a unit of measurement, the mapper 500 sets it to a default value. The first value mapping component 504, the second value mapping component 506, and the third value mapping component 508 send the mapped data lists to the string comparator 600. The mapper 500 may be operated in accordance with the process depicted in FIG. 11.

Figure 6:
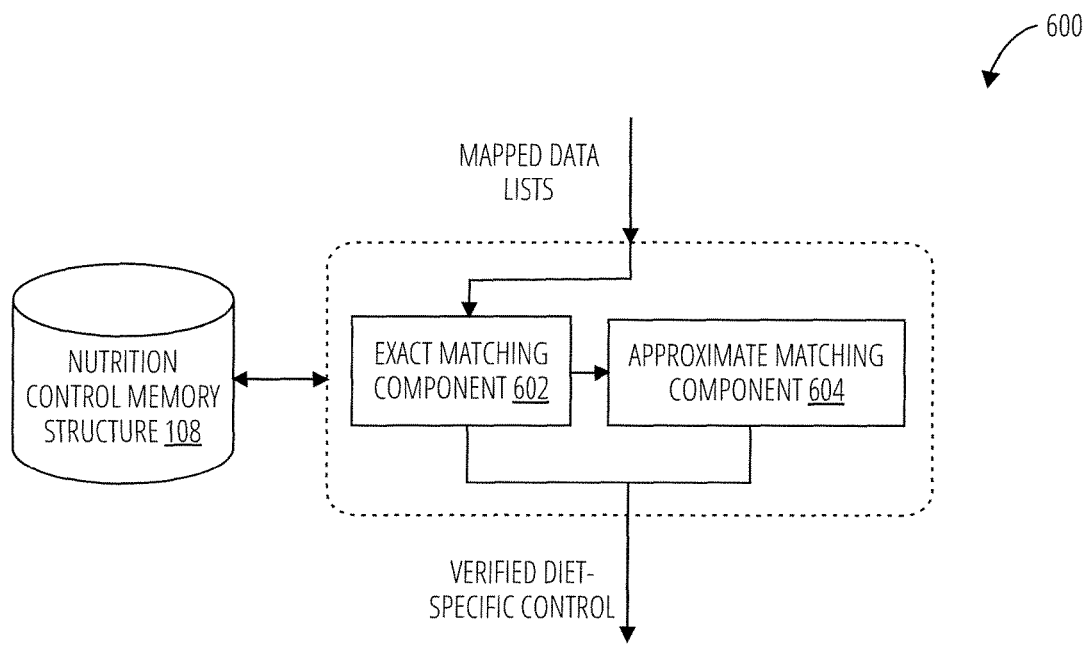
FIG. 6 illustrates an embodiment of a string comparator 600.

Referring to FIG. 6, an embodiment of a string comparator 600 comprises a nutrition control memory structure 108, an exact matching component 602, and an approximate matching component 604.

The exact matching component 602 receives the mapped data lists. The exact matching component 602 determines whether each of the food name entities comprise by the mapped data lists are present in the nutrition control memory structure 108. The exact matching component 602 receives the nutrition information control from the nutrition control memory structure 108 for those food name entities that are matched in the nutrition control memory structure 108 and generates a verified diet-specific control. The exact matching component 602 sends the verified diet-specific control to the nutrient calculator 110. The exact matching component 602 sends entities to the approximate matching component 604 if those entities are not matched in the nutrition control memory structure 108.

The approximate matching component 604 receives entities from the exact matching component 602 that do not match the nutrition control memory structure 108. The approximate matching component 604 calculates a similarity probability for each unmatched entity to those entities in the nutrition control memory structure 108. The similarity probability may be based on the longest matching block between the entities. The approximate matching component 604 may then eliminate those entities with a similarity probability below a pre-determined threshold value. The approximate matching component 604 then determines the closest matching entity. The approximate matching component 604 may utilize a Levenshtein transform to determine an edit distance between the entity in the mapped data lists and the nutrition control memory structure 108. The edit distance may be based on insertions, deletions, and substitutions. The entity with the lowest edit distance may be selected, the nutrition information control from the nutrition control memory structure 108 for that entity is received, and a verified diet-specific control is generated and sent to the nutrient calculator 110.

The pre-determined threshold value may range from 0.7 to 0.99. A lower pre-determined threshold value may result in non-related data matching (e.g., "piece" as "spice"). Increasing the pre-determined threshold value may result in non-detection (e.g., "Apple", "Apples"). A pre-determined threshold value of 0.8 may be utilized. The string comparator 600 may be operated in accordance with the process depicted in FIG. 12.

Figure 7:
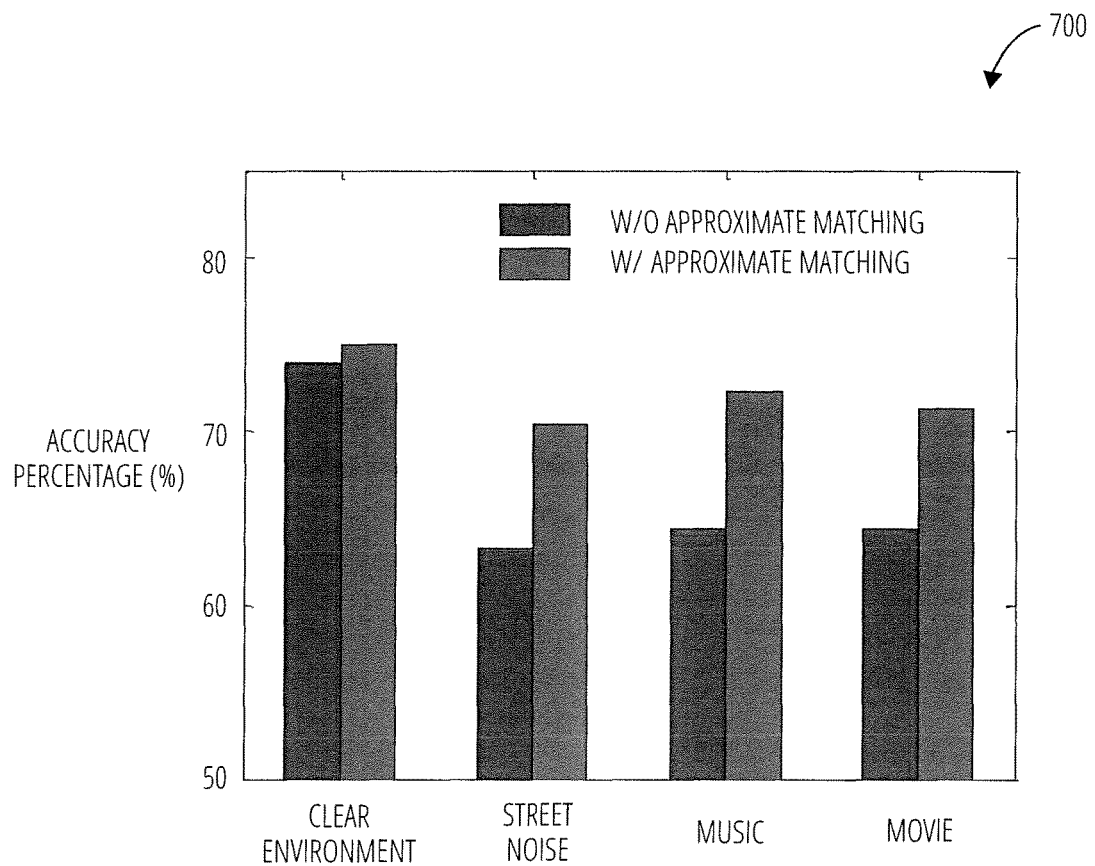
FIG. 7 illustrates an embodiment of approximate matching results 700.

Referring to FIG. 7, exemplary approximate matching results 700 are depicted for the performance of the nutritional monitoring and control system 100 with and without the presence of approximation matching. The accuracy percentage is depicted for four environments: a clear environment, street noise, music, and a movie. The results demonstrate an amount of improvement in finding Nutrition Specific data utilizing approximate matching of 7%.

Referring to FIG. 8, an embodiment of a nutrition monitoring and control method 800 receives a text, an audio, or an unstructured input (block 802). The nutrition monitoring and control method 800 determines whether the unstructured input is an audio or a text (decision block 804). If an audio, the audio is converted to a text (block 806). If a text or converted audio to text, natural language processing is performed on the text to determine the generated entity (block 808). The nutrition monitoring and control method 800 then determines whether a prompt is generated (decision block 810). A prompt may be generated if one of the required entities is not present in the text. If the prompt is generated, the client device is altered to receive an unstructured input (block 812). If the prompt is not generated, the generated entity is mapped (block 814). Once mapped, the mapped data lists are matched to a nutrition item (block 816). The nutrition nutrient information is then calculated (block 818). Based on the nutrition nutrient information, a diet planning action is determined (block 820).

Referring to FIG. 9, an exemplary NLP method 900 receives a text (block 902). The NLP method 900 determines whether the text is prompted or not (decision block 904). A prompted text is a text received resulting from a client device being altered by a prompt. If the text is prompted, the original text that generated the prompt is updated (block 906). The NLP method 900 determines whether the updated text is in response to an intent prompt or an entity prompt (decision block 908). If an intent prompt or the text was not in response to a prompt, the text is matched to an intent (block 910). The NLP method 900 determines whether an intent match is found (decision block 912). If so or if the text was updated for an entity, the text is matched to entities (block 914). The required entities are then received (block 916). The NLP method 900 determines whether the required entities are matched (decision block 918). If the entities are not matched or the intent was not matched, a prompt activation signal is generated (block 920). The prompt activation signal is then sent to the prompting module (block 922). If the entities are matched, a generated entity is generated (block 924) and sent to a mapper (block 926).

Figure 10:
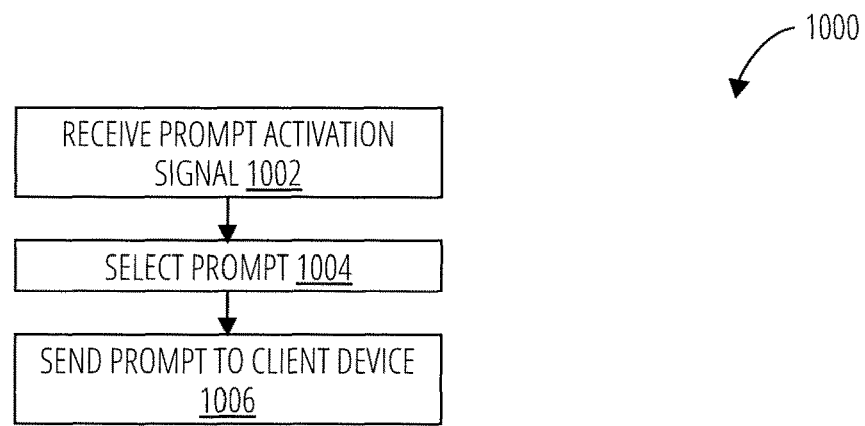
FIG. 10 illustrates an embodiment of a prompting method 1000.

Referring to FIG. 10, the prompting method 1000 receives a prompt activation signal (block 1002). A prompt is then selected (block 1004). The prompt may be selected based on whether an intent or required entity is not detected, and which required entity is not detected. A prompt is the sent to a client device (block 1006).

Figure 11:
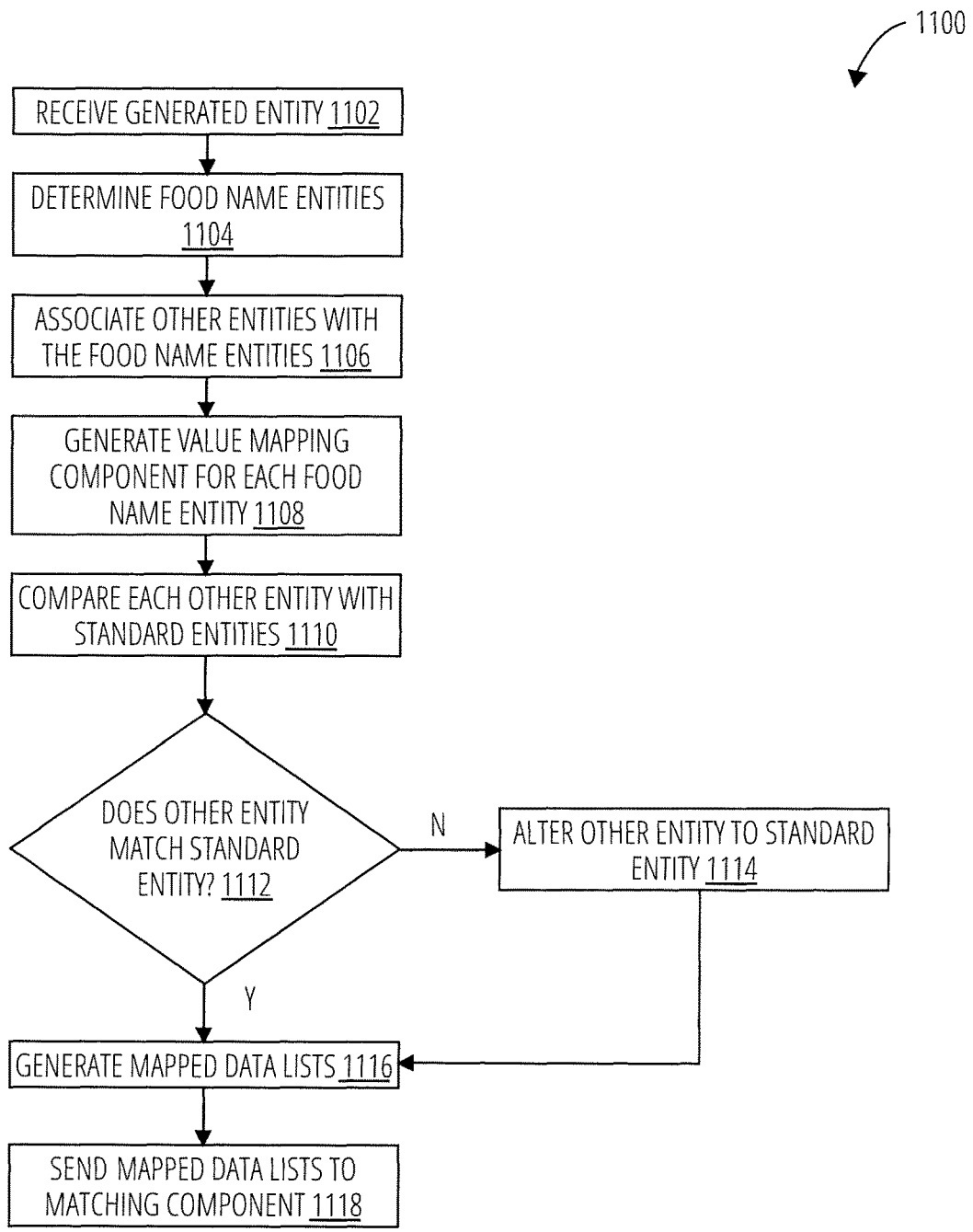
FIG. 11 illustrates an embodiment of a mapping method 1100.

Referring to FIG. 11, an exemplary mapping method 1100 receives the generated entity (block 1102). The food name entities are determined from the generated entity (block 1104). The other entities in the generated entity are associated with the food name entities (block 1106). A value mapping component is generated for each food name entity (block 1108). Each other entity is compared to a standard entity (block 1110). The one or more list dictionaries associated with the food name entities may be utilized to determine the standard entities. The mapping method 1100 determines whether each other entity associated with a food name entity matches a standard entity (decision block 1112). If not, the other entity is altered to a standard entity (block 1114). Each standard entity is associated with one or more synonymous entities. The unmatched other entity is matched to a synonymous entity. The unmatched other entity is then altered to the standard entity associated with the synonymous entity. A mapped data lists is generated (block 1116). The mapped data lists comprises the food name entities associated with a matched other entity or a standard entity. The mapped data lists are sent to the matching component (block 1118).

Figure 12:
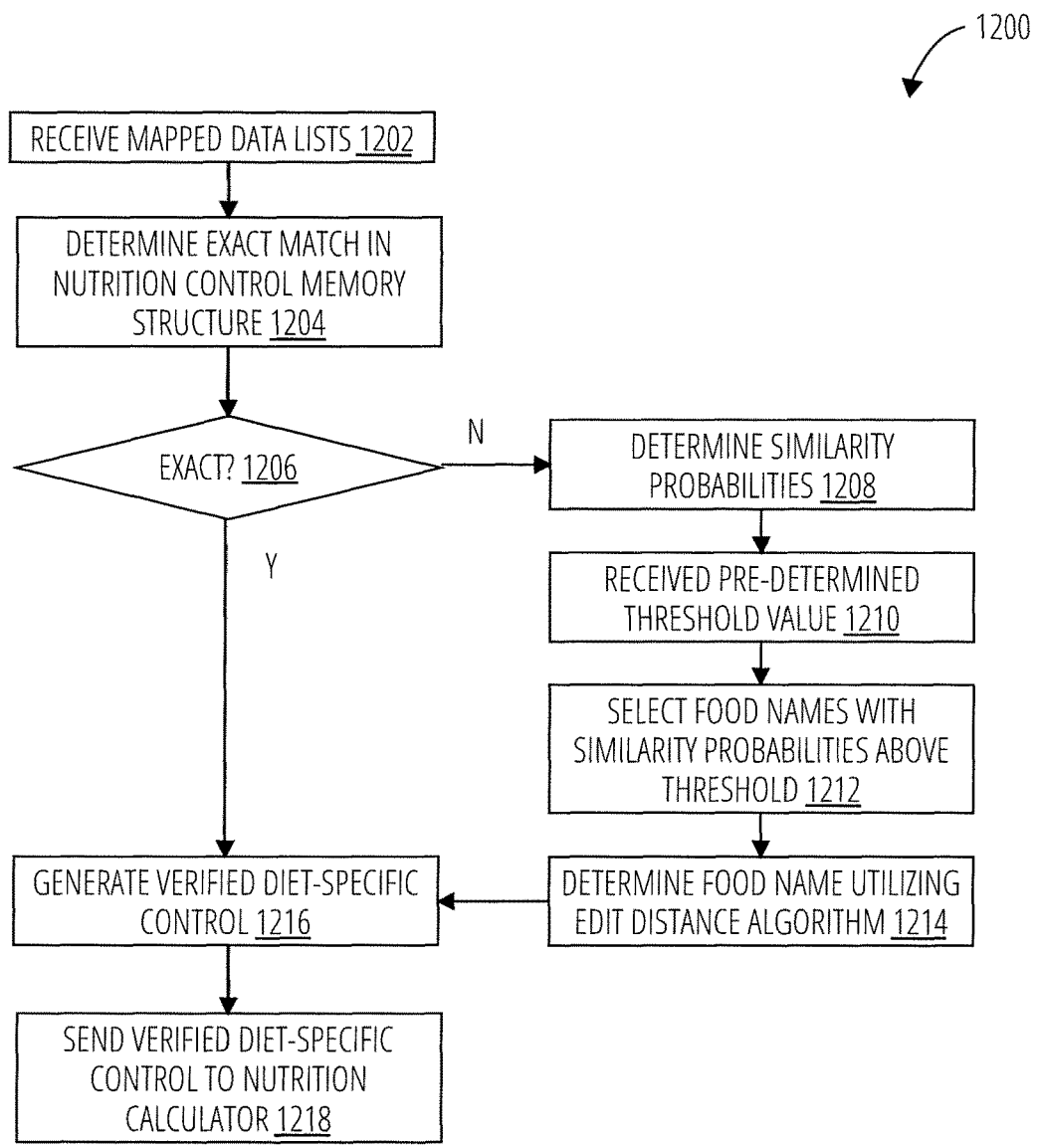
FIG. 12 illustrates an embodiment of a matching method 1200.

Referring to FIG. 12, an exemplary matching method 1200 receives the mapped data lists (block 1202). An exact match is determined for each food name entity in the nutrition control memory structure (block 1204). The matching method 1200 determines whether an exact match was determined (decision block 1206). If not, similarity probabilities are determined for each non-exact food name entity compared to the food name entities in the nutrition control memory structure (block 1208). The similarity probability may be based on the longest matching block between the entities. A pre-determined threshold value is then received (block 1210). The pre-determined threshold value may be a decimal value between 0 and 1. The food name entities in the nutrition control memory structure with a similarity probability above the pre-determined threshold value are selected (block 1212). The food name entity is determined based on edit distance (block 1214). The edit distance may be based on the Levenshtein transform, utilizing insertions, deletions, and substitutions. The food name entity with the lowest edit distance may be selected. A verified diet specific signal is generated (block 1216). The verified diet-specific control comprises the food name entities and associated nutritional information from the nutrition control memory structure. The verified diet-specific control is sent to the nutrition calculator (block 1218).

Figure 13:
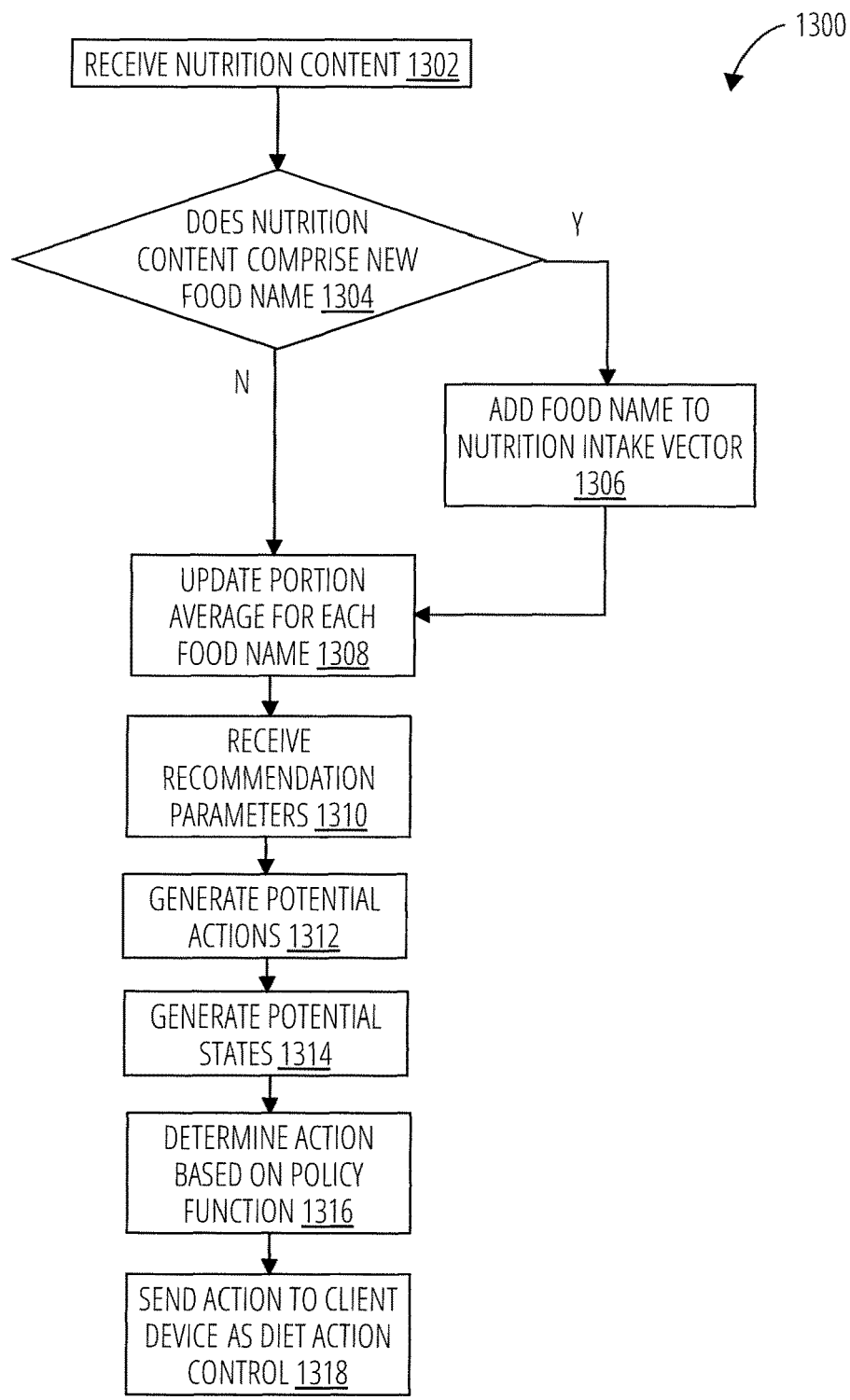
FIG. 13 illustrates an embodiment of a reinforcement learning diet recommendation method 1300.

Referring to FIG. 13, an exemplary reinforcement learning diet recommendation method 1300 receives nutrition content (block 1302). The nutrition content may be received from the nutrient calculator 110. The nutrition content may comprise a food name and a portion size. The reinforcement learning diet recommendation method 1300 determines if the nutrition content comprises a new food name (decision block 1304). A nutrition intake vector, which may be a subset of the nutrition control memory structure 108, may be stored and compared to determine if the nutrition content comprises a new food name. If so, the food name is added to the nutrition intake vector (block 1306). If the food name is not a new food name, or if the food name is added to the nutrition intake vector, the portion average is updated for each food name in the nutrition intake vector (block 1308). Recommendation parameters are received (block 1310). The recommendation parameters may include a calorie goal (calGoal), sub-goals based on the calorie goal, a learning rate ($\alpha$), a discount rate ($\gamma$), calorie constraints (calorieConstraints), and rewards. The potential actions (block 1312) and the potential states (block 1314) are generated. An action is determined from the potential actions based on the policy function (block 1316). The policy for reinforcement learning problem can be learned utilizing 4 different RL methods, including SARSA, Q-Learning, Monte Carlo, and $\lambda$-SARSA. The action is sent to the client device as a diet action control (block 1318). The policy function may generate a sequence of actions, the action sent to the client device being the first action in the sequence of actions.

In some embodiments, the calorie goal is determine by a user input. The calorie goal may also be pre-determined value. The learning rate may be a value between 0 and 1. The discount factor may be a value between 0 and 1. Calorie constraints may be pre-determined values. The reward in one embodiment may be determined from an algorithm as follows:

$$\text{Reward} = \begin{cases} +r_1 & c_1 = \text{diff} \geq -d_1 \text{ and } \leq +d_1 \\ +r & c_2 = \text{diff} \geq -d_2 \text{ and } \leq +d_2 - c_1 \\ -r_3 & \text{otherwise} \end{cases} \quad \text{Equation 3}$$

An exemplary SARSA algorithm follows:

```
1: procedure SARSA-ALGORITHM
2: Initialize Q(s,a) arbitrarily
3: for each ei in episodes do
4:   a = ε-greedy(s, Q)
5:   for each step i ei do
6:     Take action a
7:     calculate r and s'
8:     a' = ε-greedy(s', Q)
9:     Q(s,a) ← Q(s,a) + α × (r + γ × Q(s',a') − Q(s,a))
10:    s ← s'
11:    a ← a'
12:    if s is terminal then
13:      Break
14:    end if
15:   end for
16: end for
17: end procedure
```

An exemplary Q-learning algorithm follows:

```
1: procedure Q-ALGORITHM
2: nop
3: Initialize Q(s,a) arbitrarily
4: for each ei in episodes do
5:   a = ε-greedy(s, Q)
6:   for each step i ei do
7:     Take action a
8:     calculate r and s'
9:     a' = ε-greedy(s', Q)
10:    Q(s,a) ← Q(s,a) + α × (r + γ × maxQ(s') − Q(s,a))
11:    s ← s'
12:    a ← a'
13:    if s is terminal then
14:      Break
15:   end if
```

```
16:   end for
17: end for
18: end procedure
```

An exemplary Monte Carlo algorithm follows:

```
1: procedure MC-ALGORITHM
2: nop
3: Initialize policy π(s) arbitrarily
4: Initialize Q(s,a) arbitrarily
5: Initialize Returns(s,a) to an empty list
6: Repeat forever:
7:   generate an episode using exploring starts and policy π
8:   for each (s,a) in episodes do
9:     R ← Returns following the first occurrence of s,a
10:    Append R to Returns(s,a)
11:    Q(s,a) ← average(Returns(s,a))
12:   end loop
13:   for each s in ei do
14:     a* ← argmax_a Q(s,a)
15:     for all a in A(s)
16:       if a==a*
17:         π(s,a) = 1−ε+ε/|A(s)|
18:       else
19:         π(s,a) = ε/|A(s)|
20:     end loop
21:   end loop
22: end loop
```

An exemplary Sarsa-$\lambda$ algorithm follows:

```
1: procedure Sarsaλ-ALGORITHM
2: nop
3: Initialize Q(s,a) arbitrarily
4: Initialize e(s,a) to zero for all s,a
5: Repeat for each episode:
6:   Initialize s, a
7:   for each step in episode:
8:     Take action a and observe r, s'
9:     a' = ε-greedy(s, Q)
10:    δ ← r + γ Q(s',a') − Q(s,a)
11:    e(s,a) ← (s,a)+1
12:    for all s, a:
13:      Q(s,a)←Q(s,a)+αδe(s, a)
14:    end loop
15:    s←s' and a←a'
16:    until s is terminal
17:   end loop
18: end loop
```

The reinforcement learning algorithm may be implemented to minimize:

$$\sum_{i=1}^{n} P_i - p_i \quad \text{Equation 4}$$

subject to:

$$\sum_{i=1}^{n} \text{calorie}(f_i, p_i) - \text{calorie}(f_i, P_i) > \text{calorieConst}_j \quad \text{Equation 5}$$

$$\forall j \in [0, \text{size}(\text{calorieConst})] \quad \text{Equation 6}$$

$$\sum_{i=1}^{n} \text{calorie}(f_i, p_i) \geq 0 \quad \text{Equation 7}$$

$$p_i \in [0, P_i] \quad \text{Equation 8}$$

where $P_i$ is the average over all the portion sizes associated with food name $f_i$ during the window size. Here $p_i$ is the optimized portion size corresponded to food name $f_i$. Here, calorie($f_i$, $p_i$) and calorie($f_i$, $P_i$) are the optimized calorie and calorie goal based on user data, respectively. Similar parameters and policy functions may be utilized to generate a diet action control for other nutrient values, such as protein, lipid, sugar, etc.

Figure 14:
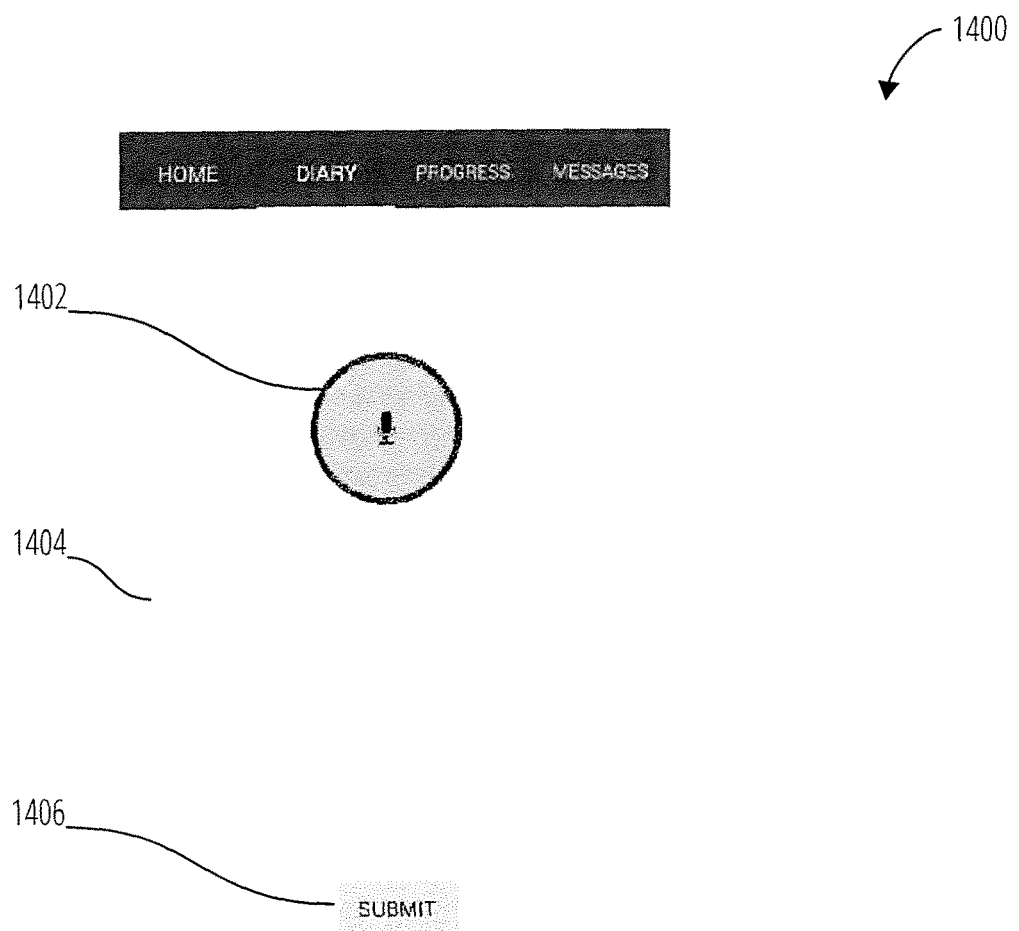
FIG. 14 illustrates an embodiment of a machine display 1400.

Referring to FIG. 14, an exemplary machine display 1400 comprises an audio input activator 1402, a text input activator 1404, and an unstructured input selector 1406.

The audio input activator 1402 may receive an input, such as a haptic input or audio input, to operate the client device to receive an audio unstructured input. The text input activator 1404 may receive an input, such as a haptic input or audio input, to operate the client device to receive an text unstructured input. The unstructured input selector 1406 may operate the client device to send the received unstructured input to the device signal switch.

Figure 15:
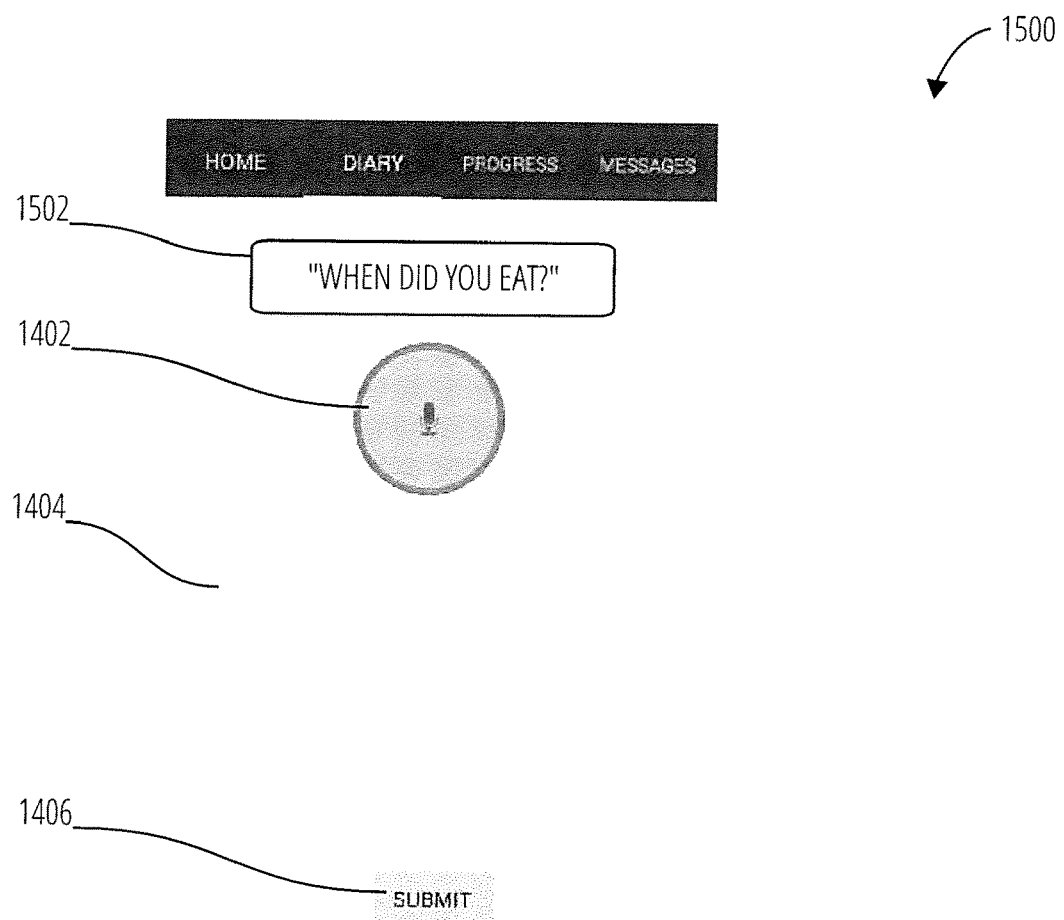
FIG. 15 illustrates an embodiment of a machine display 1500.

Referring to FIG. 15, an exemplary machine display 1500 comprises an audio input activator 1402, a text input activator 1404, an unstructured input selector 1406, and an indication of a prompt item 1502. The machine display 1500 may be configured by a client device to display the indication of a prompt item 1502 in response to receiving a prompt from the prompting module 106.

The audio input activator 1402, the text input activator 1404, and the unstructured input selector 1406 may be utilized to send a prompt item associated with the indication of a prompt item 1502 to the client device.

Figure 16:
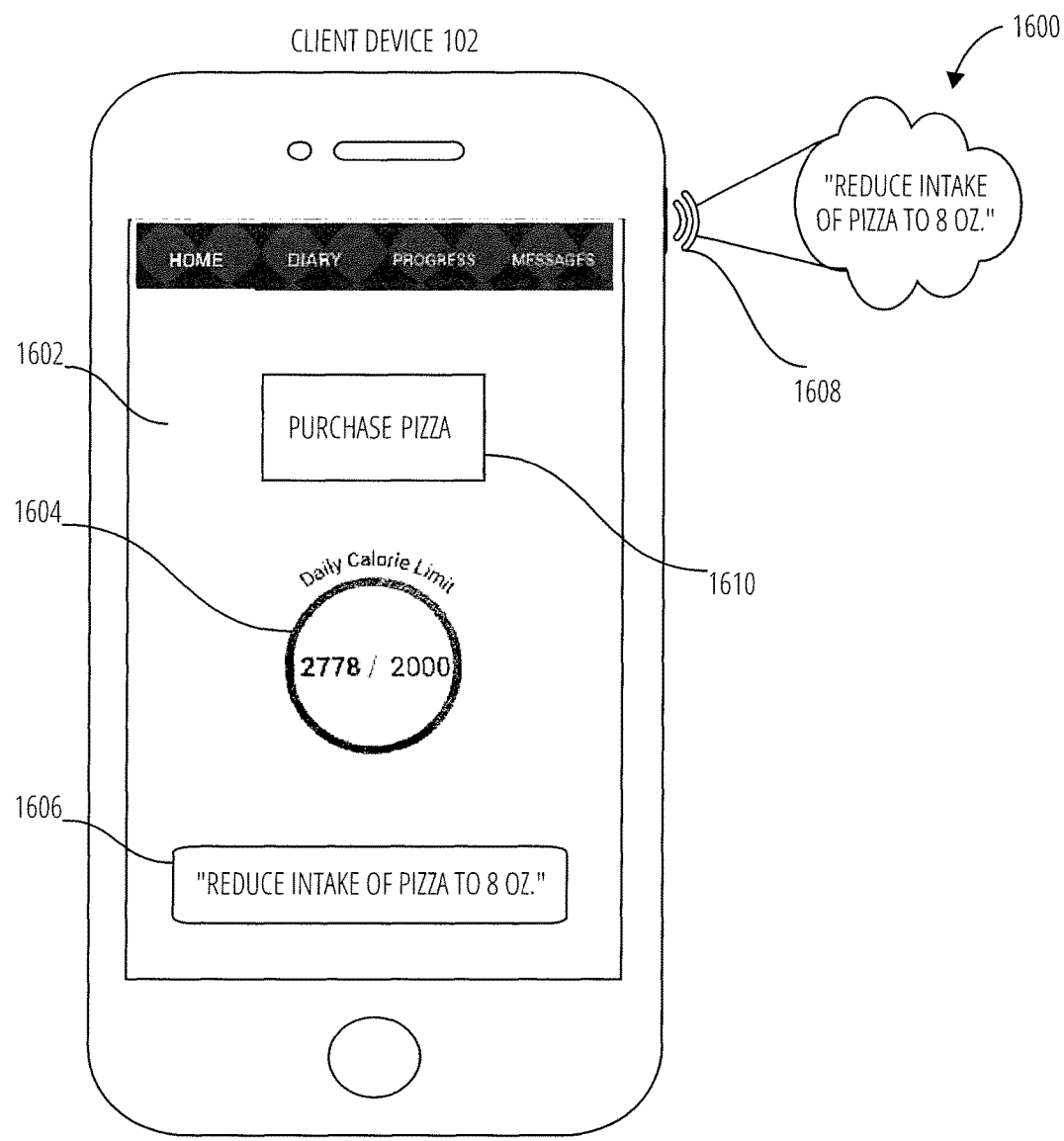
FIG. 16 illustrates an embodiment of a machine interface 1600.

Referring to FIG. 16, an exemplary machine interface 1600 comprises a client device 102, which is configured to display a machine display 1602 and emit an alert 1608. The machine display 1602 may comprise a diet planning recommendation control 1604, a text message 1606, and an action control 1610. The client device may be operated to display the machine display 1602 based on a diet action control from the diet planning module. The diet planning recommendation control 1604 may display progress toward a predetermined goal.

The text message 1606 may be displayed based on the diet action control. The text message 1606 may comprise a food name and a portion size. The alert 1608 may be emitted from the client device 102 as an audible sound. The alert 1608 may comprise a food name and a portion size. The action control 1610 may operate the client device 102 to affect a purchase of a product associated with the diet change recommendation in response to an input, such as a haptic input associated with the action control 1610 or a received audio input by the client device 102.

Figure 17:
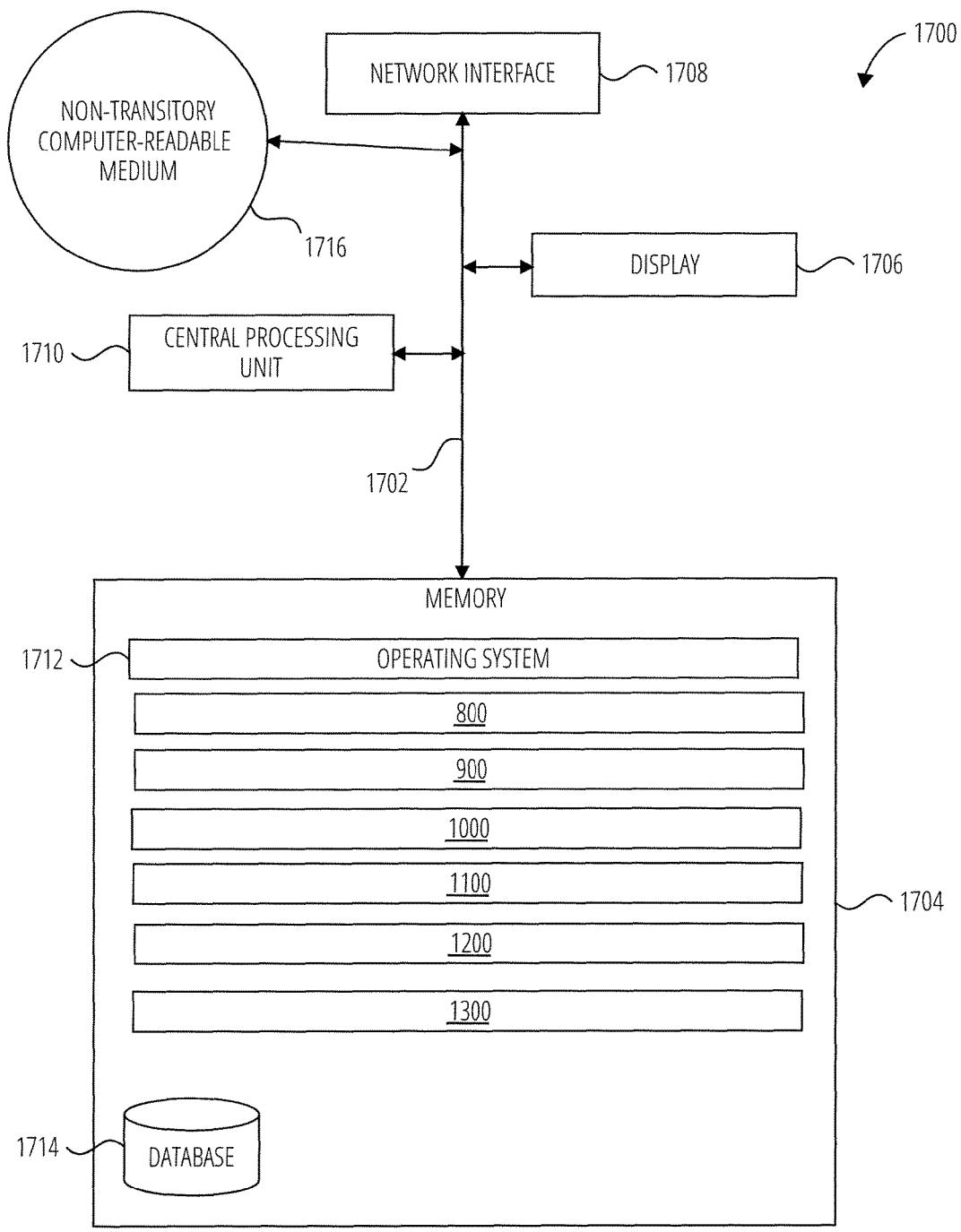
FIG. 17 illustrates a system 1700 in accordance with one embodiment.

FIG. 17 illustrates several components of an exemplary system 1700 in accordance with one embodiment. In various embodiments, system 1700 may include a desktop PC, server, workstation, mobile phone, laptop, tablet, set-top box, appliance, or other computing device that is capable of performing operations such as those described herein. In some embodiments, system 1700 may include many more components than those shown in FIG. 17. However, it is not necessary that all of these generally conventional components be shown in order to disclose an illustrative embodiment. Collectively, the various tangible components or a subset of the tangible components may be referred to herein as "logic" configured or adapted in a particular way, for example as logic configured or adapted with particular software or firmware.

In various embodiments, system 1700 may comprise one or more physical and/or logical devices that collectively provide the functionalities described herein. In some embodiments, system 1700 may comprise one or more replicated and/or distributed physical or logical devices.

In some embodiments, system 1700 may comprise one or more computing resources provisioned from a "cloud computing" provider, for example, Amazon Elastic Compute Cloud ("Amazon EC2"), provided by Amazon.com, Inc. of Seattle, Wash.; Sun Cloud Compute Utility, provided by Sun Microsystems, Inc. of Santa Clara, Calif.; Windows Azure, provided by Microsoft Corporation of Redmond, Wash., and the like.

System 1700 includes a bus 1702 interconnecting several components including a network interface 1708, a display 1706, a central processing unit 1710, and a memory 1704.

Memory 1704 generally comprises a random access memory ("RAM") and permanent non-transitory mass storage device, such as a hard disk drive or solid-state drive. Memory 1704 stores an operating system 1712.

These and other software components may be loaded into memory 1704 of system 1700 using a drive mechanism (not shown) associated with a non-transitory computer-readable medium 1716, such as a floppy disc, tape, DVD/CD-ROM drive, memory card, or the like.

Memory 1704 also includes database 1714. In some embodiments, system 1700 may communicate with database 1714 via network interface 1708, a storage area network ("SAN"), a high-speed serial bus, and/or via the other suitable communication technology.

In some embodiments, database 1714 may comprise one or more storage resources provisioned from a "cloud storage" provider, for example, Amazon Simple Storage Service ("Amazon S3"), provided by Amazon.com, Inc. of Seattle, Wash., Google Cloud Storage, provided by Google, Inc. of Mountain View, Calif., and the like.

Various terminology is used herein, and should be accorded its conventional meaning in the relevant arts unless an express definition or context indicates otherwise.

"Action control" in this context refers to a pulse or frequency of electricity or light that represents a control command as it travels over a network, a computer channel or wireless, the control command comprising instructions to alter the operation of a device to be activated by an one or more types of inputs and has a specific output associated with the type of input received, the output effecting a purchase of a product.

"Approximate matching component" in this context refers to a logic component to select a signal from a set of signals by altering each signal of the set of signals, comparing each altered signal to one or more other signals, and selecting based on the comparison.

"Associator" in this context refers to a correlator (see the definition for Correlator).

"Classifier" in this context refers to a specific type of correlator/associator logic that associates one or more inputs with a category, class, or other group sharing one or more common characteristics. An example of a classifier that may commonly be implemented in programmable hardware is a packet classifier used in network switches, firewalls, and routers (e.g., packet classifiers utilizing Ternary Content Addressable Memories). An example software or firmware classifier is: if (input1.value<12.5) input1.group=group1; else if (input1.value>=12.5 and input1.value<98.1) input1.group=group2; else input1.group=group3; Other examples of classifiers will be readily apparent to those of skill in the art, without undo experimentation.

"Combiner" in this context refers to a logic element that combines two or more inputs into fewer (often a single) output. Example hardware combiners are arithmetic units (adders, multipliers, etc.), time-division multiplexers, and analog or digital modulators (these may also be implemented is software or firmware). Another type of combiner builds an association table or structure (e.g., a data structure instance having members set to the input values) in memory for its inputs. For example: val1, val2, val3→combiner logic→{val1, val2, val3} set.val1=val1; set.val2=val2;

set.val3=val3; Other examples of combiners will be evident to those of skill in the art without undo experimentation.

"Comparator" in this context refers to a logic element that compares two or more inputs to produce one or more outputs that reflects similarity or difference of the inputs. An example of a hardware comparator is an operational amplifier that outputs a signal indicating whether one input is greater, less than, or about equal to the other. An example software or firmware comparator is: if (input1==input2) output=val1; else if (input1>input2) output=val2; else output=val3; Many other examples of comparators will be evident to those of skill in the art, without undo experimentation.

"Correlator" in this context refers to a logic element that identifies a configured association between its inputs. One examples of a correlator is a lookup table (LUT) configured in software or firmware. Correlators may be implemented as relational databases. An example LUT correlator is: |low_alarm_condition|low_threshold_value|0||safe_condition|safe_lower_bound|safe_upper_bound||high alarm_condition|high_threshold_value|0| Generally, a correlator receives two or more inputs and produces an output indicative of a mutual relationship or connection between the inputs. Examples of correlators that do not use LUTs include any of a broad class of statistical correlators that identify dependence between input variables, often the extent to which two input variables have a linear relationship with each other. One commonly used statistical correlator is one that computes Pearson's product-moment coefficient for two input variables (e.g., two digital or analog input signals). Other well-known correlators compute a distance correlation, Spearman's rank correlation, a randomized dependence correlation, and Kendall's rank correlation. Many other examples of correlators will be evident to those of skill in the art, without undo experimentation.

"Diet action control" in this context refers to a pulse or frequency of electricity or light that represents a control command as it travels over a network, a computer channel or wireless, the control command comprising instructions to alter the operation of a device to alter a machine display of the device, the instructions associated with a diet change recommendation.

"Edit distance" in this context refers to a way of quantifying how dissimilar two strings (e.g., words) are to one another by counting the minimum number of operations required to transform one string into the other.

"Entity matching component" in this context refers to a logic component to compare each of a first set of signals to a second set of signals and altering the first set of signals with one or more tags associated with the second set of signals.

"Generated entity" in this context refers to a text altered by the addition of tags associated with the entities.

"Hungarian method" in this context refers to a combinatorial optimization algorithm that solves the assignment problem in polynomial time and which anticipated later primal-dual methods.

"Incrementer" in this context refers to logic to advance (increase or decrease) a counting or index value by a fixed or predictably variable amount. Examples of hardware incrementers include adder arithmetic circuits and counter circuits. An example of a software incrementer is: x=x+incrementValue. Incrementers may be used as counters, or as logic to advance a referencial or associative index in a memory data structure.

"Intent matching component" in this context refers to a logic component to compare a string with a set of strings and select one of the string from the set of strings.

"Mapper" in this context refers to a device configured with logic to associate an entity of a string with one or more other entities of the string or matched entity.

"Module" in this context refers to a logic component having distinct inputs and outputs as illustrated in the drawings and described in the Description herein, and operating on the inputs using a described algorithm to produce the outputs.

"Nutrient calculator" in this context refers to a logic component to receive an input of an array of food name entities and associated entities and alter the array based on one or more pre-determined equations, and output the resulting array.

"Parser" in this context refers to logic that divides an amalgamated input sequence or structure into multiple individual elements. Example hardware parsers are packet header parsers in network routers and switches. An example software or firmware parser is: aFields=split("val1, val2, val3", ","); Another example of a software or firmware parser is: readFromSensor gpsCoordinate; x_pos=gpsCoordinate.x; y_pos=gpsCoordinate.y; z_pos=gpsCoordinate.z; Other examples of parsers will be readily apparent to those of skill in the art, without undo experimentation.

"Prompting module" in this context refers to a logic component to select instructions from a set of instructions based on an input, generate a control based on the selected instructions, and send the output control to another device based on the input.

"Required entities" in this context refers to a list of tags for which a "null" entity associated therewith alters the operation of the natural language processor.

"Selector" in this context refers to a logic element that selects one of two or more inputs to its output as determined by one or more selection controls. Examples of hardware selectors are multiplexers and demultiplexers. An example software or firmware selector is: if (selection_control==true) output=input1; else output=input2; Many other examples of selectors will be evident to those of skill in the art, without undo experimentation.

"Sequencer" in this context refers to logic to generate an ordered list of outputs from either an unordered or partially ordered set of inputs, or from a starting input and rules to generate next inputs. One attribute of a sequencer is that the outputs are done sequentially, meaning one after the other in time. An example of a hardware sequencer is a multiplexer with a counter driving its selection input. An example of a software or firmware sequencer is: out=val++; Other examples of hardware and software or firmware sequencers will now be readily apparent to those of skill in the relevant arts.

"Simple mapping component" in this context refers to a logic component to associate an entity of a string with one or more other entities of the string.

"Standard entity" in this context refers to an entity stored within a nutritional database, such as, the United States Department of Agriculture national database.

"Switch" in this context refers to logic to select one or more inputs to one or more outputs under control of one or more selection signals. Examples of hardware switches are mechanical electrical switches for switching power to circuits, devices (e.g., lighting), or motors. Other examples of hardware switches are solid-state switches such as transistors. An example of a hardware or firmware switch is: if (selection==true) output=input; else output=0; A somewhat more complicated software/firmware switch is: if (selection1==true and selection2==true) output=input1; else if (selection1==true and selection2==false) output=input2; else if (selection1==false and selection2==true) output=input3; else output=noOp; Switches operate similarly to selectors in many ways (see the definition of Selector), except in some cases switches may select all inputs to the output,(s) not select among inputs. Other examples of switches will be readily apparent to those having skill in the art, without undo experimentation.

"Tag" in this context refers to a string associated with a classification of entities.

"Text message" in this context refers to an electronic communication comprising one or more units of information that corresponds to a grapheme, grapheme-like unit, or symbol, such as in an alphabet or syllabary in the written form of a natural language.

"Unstructured input" in this context refers to a text or audio received by a client device to update a text previously received by a natural language processor.

"Value mapping component" in this context refers to a logic component to replace an entity of a string with a standard entity.

"Verified diet-specific control" in this context refers to a pulse or frequency of electricity or light that represents a control command as it travels over a network, a computer channel or wireless, the control command comprising an array of associated entities and their nutritional information.

"Circuitry" in this context refers to electrical circuitry having at least one discrete electrical circuit, electrical circuitry having at least one integrated circuit, electrical circuitry having at least one application specific integrated circuit, circuitry forming a general purpose computing device configured by a computer program (e.g., a general purpose computer configured by a computer program which at least partially carries out processes or devices described herein, or a microprocessor configured by a computer program which at least partially carries out processes or devices described herein), circuitry forming a memory device (e.g., forms of random access memory), or circuitry forming a communications device (e.g., a modem, communications switch, or optical-electrical equipment).

"Firmware" in this context refers to software logic embodied as processor-executable instructions stored in read-only memories or media.

"Hardware" in this context refers to logic embodied as analog or digital circuitry.

"Logic" in this context refers to machine memory circuits, non transitory machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se (however does not exclude machine memories comprising software and thereby forming configurations of matter).

"Programmable device" in this context refers to an integrated circuit designed to be configured and/or reconfigured after manufacturing. The term "programmable processor" is another name for a programmable device herein. Programmable devices may include programmable processors, such as field programmable gate arrays (FPGAs), configurable hardware logic (CHL), and/or any other type programmable devices. Configuration of the programmable device is generally specified using a computer code or data such as a hardware description language (HDL), such as for example Verilog, VHDL, or the like. A programmable device may include an array of programmable logic blocks and a hierarchy of reconfigurable interconnects that allow the programmable logic blocks to be coupled to each other according to the descriptions in the HDL code. Each of the programmable logic blocks may be configured to perform complex combinational functions, or merely simple logic gates, such as AND, and XOR logic blocks. In most FPGAs, logic blocks also include memory elements, which may be simple latches, flip-flops, hereinafter also referred to as "flops," or more complex blocks of memory. Depending on the length of the interconnections between different logic blocks, signals may arrive at input terminals of the logic blocks at different times.

"Software" in this context refers to logic implemented as processor-executable instructions in a machine memory (e.g. read/write volatile or nonvolatile memory or media).

Herein, references to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple ones. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other. Any terms not expressly defined herein have their conventional meaning as commonly understood by those having skill in the relevant art(s).

Various logic functional operations described herein may be implemented in logic that is referred to using a noun or noun phrase reflecting said operation or function. For example, an association operation may be carried out by an "associator" or "correlator". Likewise, switching may be carried out by a "switch", selection by a "selector", and so on.

Those skilled in the art will recognize that it is common within the art to describe devices or processes in the fashion set forth herein, and thereafter use standard engineering practices to integrate such described devices or processes into larger systems. At least a portion of the devices or processes described herein can be integrated into a network processing system via a reasonable amount of experimentation. Various embodiments are described herein and presented by way of example and not limitation.

Those having skill in the art will appreciate that there are various logic implementations by which processes and/or systems described herein can be effected (e.g., hardware, software, or firmware), and that the preferred vehicle will vary with the context in which the processes are deployed. If an implementer determines that speed and accuracy are paramount, the implementer may opt for a hardware or firmware implementation; alternatively, if flexibility is paramount, the implementer may opt for a solely software implementation; or, yet again alternatively, the implementer may opt for some combination of hardware, software, or firmware. Hence, there are numerous possible implementations by which the processes described herein may be effected, none of which is inherently superior to the other in that any vehicle to be utilized is a choice dependent upon the context in which the implementation will be deployed and the specific concerns (e.g., speed, flexibility, or predictability) of the implementer, any of which may vary. Those skilled in the art will recognize that optical aspects of implementations may involve optically-oriented hardware, software, and or firmware.

Those skilled in the art will appreciate that logic may be distributed throughout one or more devices, and/or may be comprised of combinations memory, media, processing circuits and controllers, other circuits, and so on. Therefore, in the interest of clarity and correctness logic may not always be distinctly illustrated in drawings of devices and systems, although it is inherently present therein. The techniques and procedures described herein may be implemented via logic distributed in one or more computing devices. The particular distribution and choice of logic will vary according to implementation.

The foregoing detailed description has set forth various embodiments of the devices or processes via the use of block diagrams, flowcharts, or examples. Insofar as such block diagrams, flowcharts, or examples contain one or more functions or operations, it will be understood as notorious by those within the art that each function or operation within such block diagrams, flowcharts, or examples can be implemented, individually or collectively, by a wide range of hardware, software, firmware, or virtually any combination thereof. Portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more processing devices (e.g., as one or more programs running on one or more computer systems), as one or more programs running on one or more processors (e.g., as one or more programs running on one or more microprocessors), as firmware, or as virtually any combination thereof, and that designing the circuitry or writing the code for the software or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, flash drives, SD cards, solid state fixed or removable storage, and computer memory.

What is claimed is:

1. An apparatus comprising:
    a natural language processor to receive text from a client device and transform the text into a generated entity;
    a mapper to transform the generated entity into mapped data lists;
    a string comparator to transform the mapped data lists into a verified diet-specific control utilizing a nutrition control memory structure;
    a nutrient calculator to determine nutrition content from the verified diet-specific control;
    a diet planning module to generate a diet action control, the diet action control comprising instructions to operate the client device to perform a diet change recommendation on the client device and apply the diet action control to the client device; and
    a prompting module to:
        receive a prompt activation signal from the natural language processor;
        generate a prompt comprising instructions to operate the client device to display on a machine display of the client device an indication of a prompt item, the prompt item comprising an intent signal or a required entity;
        receive an unstructured input, the unstructured input enabling the natural language processor to transform the text into the generated entity; and
        send the prompt to the client device.

2. The apparatus of claim 1, further comprising a speech recognition module to:
    receive an audio from the client device;
    generate the text from the audio; and
    send the text to the natural language processor.

3. The apparatus of claim 1, wherein the natural language processor comprises:
    an intent matching component to:
        compare the text to the intent signal in an intent signal control memory structure; and
        generate the prompt activation signal in response to the text not matching the intent signal; and
    an entity matching component to:
        compare the text to entity signals in an entity signal control memory structure;
        transform the text into the generated entity by associating the text with the entity signals;
        receive a list of required entities; and
        generate the prompt activation signal in response to the generated entity not comprising one or more of required entities of the list of required entities.

4. The apparatus of claim 1, further comprising a training component to:
    generate the intent signal and entity signals; and
    send the intent signal to an intent signal control memory structure and the entity signals to an entity signal control memory structure.

5. The apparatus of claim 4, wherein the training component generates the intent signal and the entity signals from the text.

6. The apparatus of claim 1, wherein the mapper further comprises:
    a simple mapping component to:
        associate food name entities in the generated entity with other entities in the generated entity; and
    a value mapping component to:
        compare the other entities associated with each of the food name entities to a standard entity in one or more list dictionaries; and
        alter the other entities into the standard entity in response to the other entities being one of one or more synonymous entities to the standard entity.

7. The apparatus of claim 1, the string comparator further to:
    determine whether food name entities in the mapped data lists match the nutrition control memory structure; and
    in response to one or more of the food name entities not matching the nutrition control memory structure, utilizing an approximate matching component to determine the verified diet-specific control.

8. The apparatus of claim 7, the approximate matching component further to:
- determine a similarity probability of the one or more of the food name entities to the verified diet-specific control in the nutrition control memory structure;
- receive a pre-determined threshold value;
- determine an edit distance of the verified diet-specific control to the one or more of the food name entities for the verified diet-specific control greater than the pre-determined threshold value; and
- select the verified diet-specific control with the edit distance that is a lowest value.

9. The apparatus of claim 1, wherein the diet action control affects the client device to display a text message on the machine display associated with the diet change recommendation.

10. The apparatus of claim 1, wherein the diet action control affects the client device to emit an audible alert associated with the diet change recommendation.

11. The apparatus of claim 1, wherein the diet action control affects the client device to display an action control on the machine display, the action control to:
- receive an input; and
- in response to the input, effect a purchase of a product associated with the diet change recommendation.

* * * * *